US010745443B2

(12) United States Patent
Wisniewski et al.

(10) Patent No.: US 10,745,443 B2
(45) Date of Patent: Aug. 18, 2020

(54) VASOPRESSIN-2 RECEPTOR AGONISTS

(71) Applicant: Ferring B.V., Hoofddorp (NL)

(72) Inventors: Kazimierz Wisniewski, San Diego, CA (US); Claudio Schteingart, San Diego, CA (US); Pierre Riviere, San Diego, CA (US)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 16/145,073

(22) Filed: Sep. 27, 2018

(65) Prior Publication Data

US 2019/0194257 A1 Jun. 27, 2019

Related U.S. Application Data

(63) Continuation of application No. 14/647,357, filed as application No. PCT/US2014/048317 on Jul. 25, 2014, now Pat. No. 10,131,692.

(60) Provisional application No. 61/859,024, filed on Jul. 26, 2013, provisional application No. 61/952,073, filed on Mar. 12, 2014.

(51) Int. Cl.
*C07K 7/54* (2006.01)
*C07D 417/06* (2006.01)
*C07K 7/16* (2006.01)
*A61K 38/00* (2006.01)

(52) U.S. Cl.
CPC ............ *C07K 7/54* (2013.01); *C07D 417/06* (2013.01); *C07K 7/16* (2013.01); *A61K 38/00* (2013.01)

(58) Field of Classification Search
None
See application file for complete search history.

(56) References Cited

U.S. PATENT DOCUMENTS

| 4,482,486 A | 11/1984 | Brtnik et al. |
| 5,698,516 A | 12/1997 | Anders et al. |

FOREIGN PATENT DOCUMENTS

| BE | 896504 A | 8/1983 | |
| CZ | 292131 | 8/2003 | |
| EP | 0037516 A1 * | 10/1981 | ............... C07K 7/16 |
| WO | WO-95/01373 A1 | 1/1995 | |

OTHER PUBLICATIONS

Jost et al., "Synthesis and some biological activities of analogues of deamino-vasopressin with the disulphide bridge altered to a thioether bridge." Collection Czechoslov. Chem. Commun. (1974) vol. 39, pp. 2835-2856.

Callahan et al., "Structure-activity relationships of novel vasopressin antagonists containing c-terminal diaminoalkanes and (aminoalkyl)guanidines." J. Med. Chem. (1989) vol. 32, pp. 391-396.
Chan et al., "Discovery and design of novel and selective vasopressin and oxytocin agonists and anagonists: the role of bioassays," Exp. Physiol (2000) 85S, pp. 7S-18S.
Czaja et al., "Analogs of arginine-vasopressin substituted in position 2 with 1-4-cl-phenylalanine or d-phenylglycine," Collect. Czech. Mech. Commun. (1993) vol. 58, pp. 675-680.
Manning et al., "C-Terminal deletions in agonistic and antagonistic analogs of vasopressin that improve their specificity for antidiuretic (v2) and vasopressor(v1) receptors," J. Med. Chem (1987), vol. 30, pp. 2245-2253.
Agerso et al., "Pharmacokinetics and renal excretion of desmopressin after intravenous administration to healthy subjects and renally impaired patients," British Journal of Clinical Pharmacology, (2004), vol. 58, No. 4, pp. 352-358.
Berge et al., "Pharmaceutical Salts," J. Pharm. Sci. (1977) vol. 66, No. 1.
Bisello et al., "Parathyroid hormone-receptor interactions identified directly by photocross-linking and molecular modeling studies," J. Biol. Chem., (1998), vol. 273, pp. 22498-22505.
Boss et al., "Induction of NFAT-mediated transcription by Gq-couples receptors in lymphoid and non-lymphoid cells," J. Biol. Chem.. (1996) vol. 271, No. 18, pp. 10429-10432.
Callreus et al., "Pharmacokinetics and antidiuretic effect of a new vasopressin analogue (F992) in overhydrated male volunteers," Eur. J. Clin. Pharmacol., (1999) vol. 55, pp. 293-298.
Favory et al., "Investigational vasopressin receptor modulators in the pipeline," Expert Opinion, (2009), vol. 18, No. 8, pp. 1119-1131.
Fjellesta-Paulsen et al., "Pharmacokinetics of 1-deamino-8-D-arginine vasopressin after various routes of administration in healthy volunteers," Clinical Endocrinology, (1993), pp. 177-182.
Hernando et al., "Immunohistochemical Localization of the Vasopressin V1b Receptor in the Rat Brain and Pituitary Gland: Anatomical Support for Its Involvement in the Central Effects of Vasopressin," Endocrinology, (2001), pp. 1659-1668.
International Search Report and Written Opinion in International Application No. PCT/US2014/048317, dated Oct. 27, 2014 (2014), 9 pages.
International Preliminary Report on Patentability in International Application No. PCT/US2014/048317, dated Jan. 26, 2016, 6 pages.
Merrifield, "Solid Phase Peptitde Synthesis, I. The Synthesis of a Tetrapeptide," J. Am. Chem. Soc., (1963) vol. 85, pp. 2149-2154.
Ostrowski et al., "Cellular Localization of Vasopressin V1a Receptor Messenger Ribonucleic Acid in Adult Male Rat Brain, Pineal, and Brain Vasculature, "Endocrinology, (1994), pp. 1511-1528.
Ruzicka et al., "Pharmacokinetics and Antidiuretic Effect of High-Dose Desmopressin in Patients with Chronic Renal Failure," Pharmacology & Toxicology, (2003) vol. 92, pp. 137-142.
Zingg, "Vasopressin and Oxytocin Receptors," Bailliere's Clinical Endocrinology and Metabolism, (1996) pp. 75-96.

* cited by examiner

*Primary Examiner* — Fred H Reynolds
(74) *Attorney, Agent, or Firm* — Foley & Lardner LLP

(57) ABSTRACT

Vasopressin-2 receptor agonists, pharmaceutical compositions thereof and methods for using the foregoing for treating diabetes insipidus, primary nocturnal enuresis, and nocturia.

8 Claims, No Drawings
Specification includes a Sequence Listing.

VASOPRESSIN-2 RECEPTOR AGONISTS

RELATED APPLICATIONS

This application is a continuation application of U.S. application Ser. No. 14/647,357, filed May 26, 2015, which is a U.S. National Phase application under 35 U.S.C. § 371 of International Patent Application No. PCT/US2014/048317, filed Jul. 25, 2014, which claims the benefit of U.S. Provisional Applications 61/859,024 filed Jul. 26, 2013, and 61/952,073 filed Mar. 12, 2014, all of which are hereby incorporated by reference in their entirety.

SEQUENCE LISTING

This instant application contains a Sequence Listing which has been submitted electronically in ASCII format and is hereby incorporated by reference in its entirety. Said ASCII copy, created on Mar. 2, 2016, is named 27521-0082US1_SL.txt and is 713 bytes in size.

FIELD

The present invention relates to novel compounds with agonist activity at the vasopressin-2 ($V_2$) receptor, pharmaceutical compositions comprising these, and use of the compounds for the manufacture of medicaments for treatment of diseases.

BACKGROUND

There are three known subtypes of vasopressin receptors, $V_{1a}$, $V_{1b}$ and $V_2$. The $V_{1b}$ receptor is also known as the $V_3$ receptor and the $V_{1a}$ receptor is also known as the $V_1$ receptor. Each subtype has a distinct pattern of expression in tissues, with $V_2$ found primarily in the kidney, where it mediates the antidiuretic activity of the endogenous ligand vasopressin (Favory et al, 2009). $V_{1b}$ is widely distributed in the brain (Hernando et al., 2001). $V_{1a}$ is found in a variety of tissues, including smooth muscle, liver, kidney, platelets, spleen and brain (Zingg, 1996; Ostrowski et al., 1994).

Agonists of the $V_2$ receptor are clinically useful. Desmopressin is a $V_2$ receptor agonist that is approved in some territories for treatment of diabetes insipidus, primary nocturnal enuresis, nocturia, and coagulation disorders including haemophilia A and von Willebrand's disease. Desmopressin binds and activates both the $V_2$ and $V_{1b}$ receptors, with weaker activity on the $V_{1a}$.

Desmopressin has been shown to be partly excreted via the kidneys (e.g. Fjellestad-Paulsen et al., 1993), and the half-life of desmopressin is increased in patients with renal impairment (Ruzicka, et al. 2003; Agersoe et al. 2004). Agersoe et al. suggest that the increased half-life might lead to prolonged antidiuretic effects and increase the risk of hyponatremia, a drop in serum sodium levels that can lead to adverse events such as seizures or coma. They further state that "although desmopressin appears to be safe and well-tolerated by patients with impaired renal function, great caution should be exercised when titrating towards an efficient dosing regimen, if patients with moderately or severe renal function are to be treated with desmopressin at all."

Therefore, there is a need for additional $V_2$ receptor agonists with reduced activity at the $V_{1b}$ receptor. Additionally, $V_2$ receptor agonists that do not rely as heavily on the kidneys for elimination may also be desirable.

SUMMARY

In one embodiment, a compound is provided according to formula I or a pharmaceutically acceptable salt thereof,

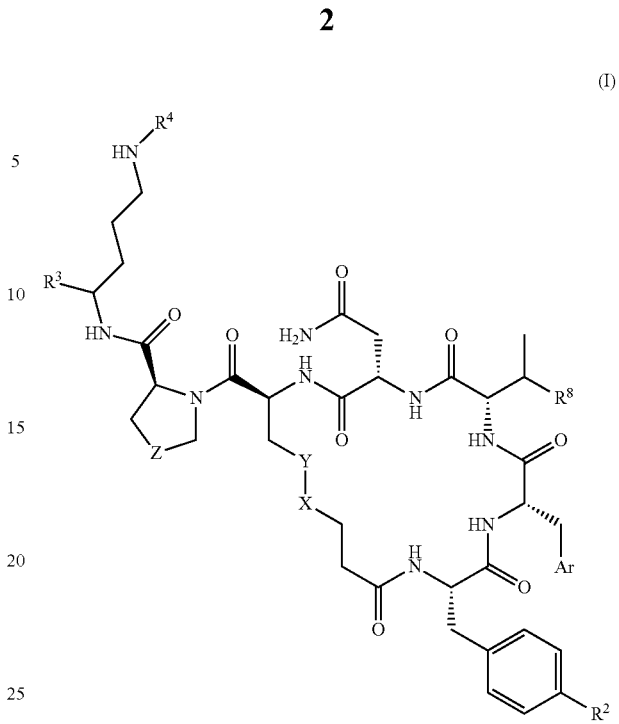

(I)

wherein $R^2$ is H, $C_1$-$C_4$ alkyl, halogen, —OH or —O—$C_1$-$C_4$ alkyl;
$R^3$ is H or —$CH_2$—OH or —C(O)—$NR^5R^6$;
$R^4$ is H or —C(=NH)—$NH_2$;
$R^5$ and $R^6$ are independently H, $C_1$-$C_6$ alkyl, —$CH_2$-cyclopropyl, -cyclopropyl or arylalkyl with the proviso that $R^5$ and $R^6$ are not both H;
X and Y are independently —$CH_2$— or —S— with the proviso that if X is —$CH_2$—, Y is not —$CH_2$—;
Z is —$CHR^7$— or S and $R^7$ is H or $C_1$-$C_4$ alkyl, halogen, —OH or —O—$C_1$-$C_4$ alkyl;
$R^8$ is H or —$CH_3$; and
Ar is heteroaryl or phenyl optionally substituted with one $C_1$-$C_4$ alkyl, halogen, —OH or —O—$C_1$-$C_4$ alkyl.

In some embodiments, $R^5$ and $R^6$ are independently H, $C_1$-$C_6$ alkyl, or arylalkyl.

In some embodiments, $R^5$ and $R^6$ are independently H, $C_1$-$C_6$ alkyl or arylalkyl.

In some embodiments, $R^5$ and $R^6$ are not both H.

In some embodiments, only one of X and Y is —S—. In some embodiments, X is —$CH_2$—. In some embodiments, X and Y are both —S—.

In some embodiments, Ar is thiophene.

In some embodiments, $R^8$ is —$CH_3$.

In some embodiments, $R^3$ is —C(O)—$NR^5R^6$. In certain of these embodiments, $R^5$ is H and $R^6$ is $C_1$-$C_4$ alkyl. In certain of these embodiments, both of $R^5$ and $R^6$ is —$CH_2CH_3$.

In some embodiments, $R^2$ is a halogen. In certain of these embodiments, $R^2$ is —Cl. In certain of these embodiments, $R^2$ is —F.

Also provided herein, according to an embodiment, is a method of treating one of diabetes insipidus, primary nocturnal enuresis, and nocturia comprising administering a therapeutically effective amount of a compound according to formula I to a patient in need thereof. The invention also includes use of the compounds described herein in treating the conditions described herein, along with use of the compounds described herein in the manufacture of a medicament for treating the conditions described herein.

According to an embodiment, the compound of formula I is used in a medicament for the treatment of diabetes insipidus, primary nocturnal enuresis, or nocturia.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry* $5^{th}$ *Ed.* Vols. A and B, Plenum Press, New York. The practice of the present invention will employ, unless otherwise indicated, conventional methods of synthetic organic chemistry, mass spectroscopy, preparative and analytical methods of chromatography, protein chemistry, biochemistry and pharmacology, within the skill of the art.

"Alkyl" is a $C_{1-12}$ straight, or branched chain alkyl. Branched alkyl include iso-, sec-, and tert-configurations.

"Aryl" is mono- or bi-cyclic aromatic carbocyclic ring system of 5-12 carbon atoms optionally substituted with $C_1$-$C_4$ alkyl, halogen, —OH or —O—$C_1$-$C_4$ alkyl. Exemplary mono- and bi-cyclic aromatic carbocyclic ring systems include optionally substituted phenyl and optionally substituted naphthyl.

"Arylalkyl" is an alkyl group which has as a substituent an aryl or heteroaryl group.

"Heteroaryl" is an aromatic heterocyclic five- or six-membered ring system optionally substituted with $C_1$-$C_4$ alkyl, halogen, —OH or —O—$C_1$-$C_4$ alkyl. A five-membered heteroaromatic ring system is a monocyclic aromatic ring system having five ring atoms, wherein 1, 2, 3 or 4 ring atoms are independently selected from N, O and S. Exemplary five-membered heteroaromatic ring systems include optionally substituted imidazolyl, thiazolyl, thienyl, furyl, pyrazolyl, and triazolyl. A six-membered heteroaromatic ring system is a monocyclic aromatic ring system having six ring atoms, wherein 1, 2, 3 or 4 ring atoms are independently selected from N, O and S. Exemplary six-membered heteroaromatic ring systems include optionally substituted pyridyl, pyrimidyl and pyrazinyl.

One embodiment of the invention provides a pharmaceutical composition comprising compounds of the invention. In a first embodiment, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases. A thorough discussion of pharmaceutically acceptable excipients and salts is available in Remington's Pharmaceutical Sciences, 18th Edition (Easton, Pa.: Mack Publishing Company, 1990).

Examples of pharmaceutically acceptable salts include acid addition salts, e.g. a salt formed by reaction with hydrohalogen acids such as hydrochloric acid and mineral acids, such as sulphuric acid, phosphoric acid and nitric acid, as well as aliphatic, alicyclic, aromatic or heterocyclic sulphonic or carboxylic acids such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid and naphthalenesulphonic acid. (see, e.g., Berge et al., *J. Pharm. Sci.* 66:1 19, 1977 and Wermuth, C. G. and P. H. Stahl, eds. Pharmaceutical Salts: Properties, Selection and Use. Zürich: *Verlag Helvetica Chimica Acta,* 2002).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule non-aqueous solution, suspension or syrup. Tablets and capsules are preferred oral administration forms. In some embodiments, the tablet is a wafer, e.g., a fast-melt wafer. In some embodiments, the wafer is administered via a sublingual route of administration. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

The dosages for therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the therapy. In some embodiments, an intravenous dose is around 100 ng. In some embodiments, an oral dose is from 1 μg to 1 mg. In some embodiments, a nasal dose is from 3 mg to 6 mg.

Abbreviations used are:

| Abbreviation | Definition |
| --- | --- |
| Ac | Acetyl |
| AcOH | Acetic acid |
| AVP | Arginine Vasopressin<br>Cys-Tyr-Phe-Gln-Asn-Cys-Pro-Arg-Gly-NH$_2$ with disulfide bridge between Cys (SEQ ID NO: 1)<br>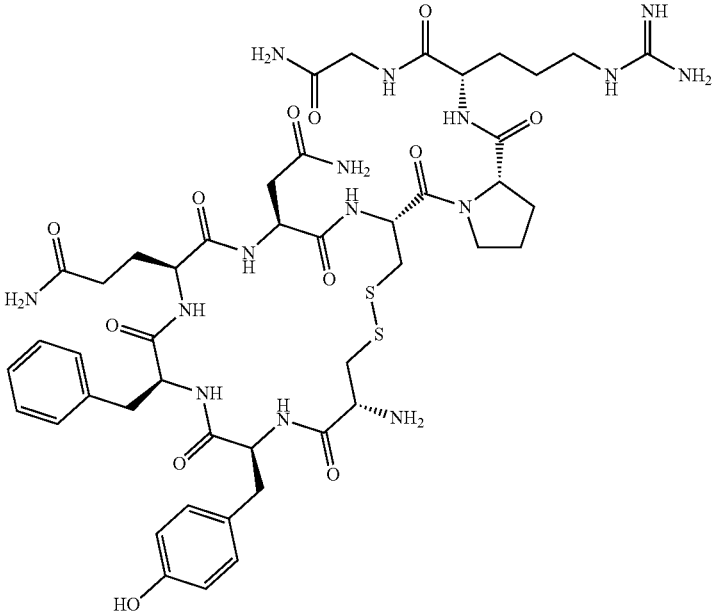 |
| BTA | N,O-Bis(trimethylsilyl)acetamide |
| Bu | butyl - alkyl residues may be further denoted as n (normal, i.e. unbranched), i (iso), s (sec) and t (tertiary) |
| Bzl | Benzyl |
| CH$_3$CN | Acetonitrile |
| DCE | 1,2-dichloroethane |
| DCM | Dichloromethane |
| dDAVP | Desmopressin, [1-deamino, 8-D-arginine]-vasopressin<br>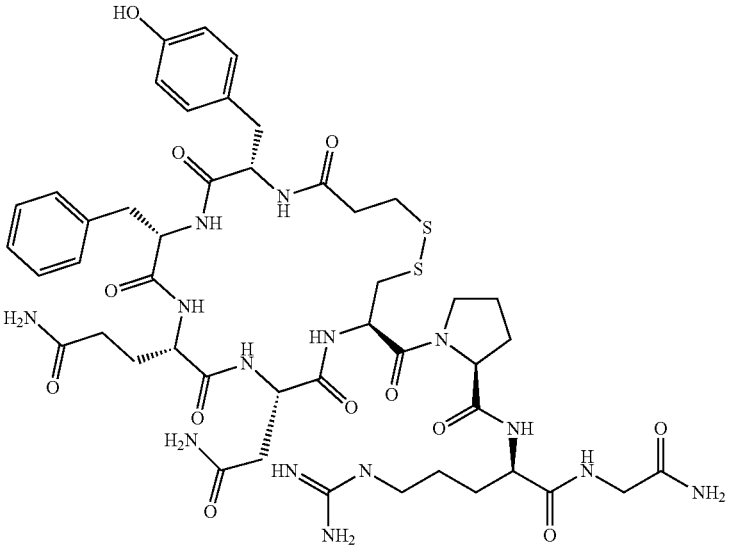 |

-continued

| Abbreviation | Definition |
|---|---|
| DIC | N,N'-Diisopropylcarbodiimide |
| DIPEA | N,N-diisopropylethylamine |
| DMF | N,N-dimethylformamide |
| dVP | 1-deamino-vasopressin |

[Structure of 1-deamino-vasopressin]

| | |
|---|---|
| Et | Ethyl |
| Fmoc | 9-fluorenylmethoxycarbonyl |
| HBTU | O-Benzotriazole-N,N,N',N'-tetramethyl-uronium,hexafluoro-phosphate |
| HFIP | 1,1,1,3,3,3-hexafluoro-2-propanol |
| HOBt | N-hydroxybenzotriazole |
| HPLC | high performance liquid chromatography |
| iBu | iso-butyl |
| cPr | cyclopropyl |
| iPr | iso-propyl |
| LC | liquid chromatography |
| Me | methyl |
| MeOH | methanol |
| MS | mass spectrometry |
| NMM | N-methylmorpholine |
| Pbf | 2,2,4,6,7-pentamethyldihydrobenzofuran-5-sulfonyl |
| tBu | tert-butyl |
| tBuOH | tert-butylalcohol |
| TFA | trifluoroacetic acid |
| TIS | triisopropylsilane |
| TMOF | Trimethyl orthoformate, trimethoxymethane |
| Trt | trityl [triphenylmethyl, $(C_6H_5)_3C-$] |

Unless otherwise specified, L-amino acids were used and conventional amino acid terminology is used. Examples of amino acids other than the twenty conventional amino acids include:

| Abbreviation | Conventional Name |
|---|---|
| Thi | β-(2-thienyl)alanine |
| Cpa | β-(4-chlorophenyl)alanine |
| Fpa | β-(4-fluorophenyl)alanine |
| Hyp | 4-Hydroxyproline |
| Thz | 1,3-thiazolidine-4-carboxylic acid, thioproline |
| Abu | 2-aminobutyric acid |
| Agm | Agmatine, (4-aminobutyl)guanidine |
| Phe(4-Me) | β-(4-methylphenyl)alanine |
| Phe(4-Et) | β-(4-ethylphenyl)alanine |

Compounds

The compounds of the invention have a structure of formula I:

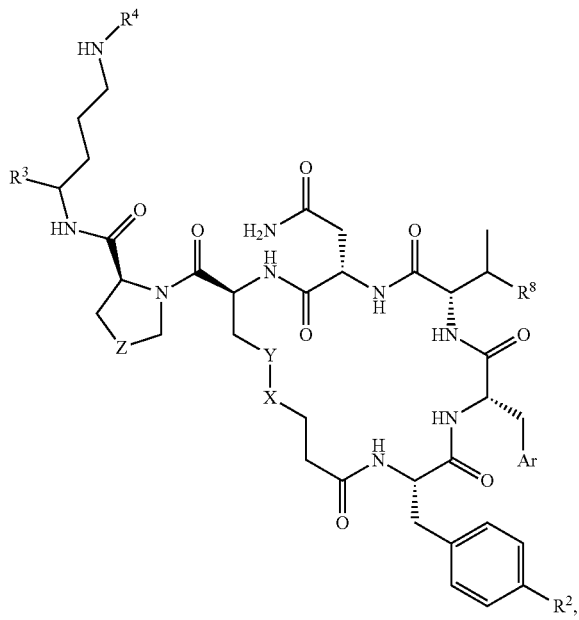

and pharmaceutically acceptable salts thereof, wherein:

$R^2$ is H, $C_1$-$C_4$ alkyl, halogen, —OH or —$C_1$-$C_4$ alkyl;

$R^3$ is H or —$CH_2$—OH or —C(O)—$NR^5R^6$;

$R^4$ is H or —C(=NH)—$NH_2$;

$R^5$ and $R^6$ are independently H, $C_1$-$C_6$ alkyl, —$CH_2$-cyclopropyl, -cyclopropyl or arylalkyl with the proviso that $R^5$ and $R^6$ are not both H;

X and Y are independently —$CH_2$— or S with the proviso that if X is —$CH_2$—, Y is not —$CH_2$—;

Z is —$CHR^7$— or S and $R^7$ is H or $C_1$-$C_4$ alkyl, halogen, —OH or —O—$C_1$-$C_4$ alkyl;

$R^8$ is H or —$CH_3$;

Ar is heteroaryl or phenyl optionally substituted with one $C_1$-$C_4$ alkyl, halogen, —OH or —O—$C_1$-$C_4$ alkyl.

TABLE 1

Example Compounds of the Invention.

| Compound | $R^2$ | $R^3$ (configuration) | $R^4$ | Ar | X | Y | Z |
|---|---|---|---|---|---|---|---|
| 1 | Cl | $CH_2OH$ (R) | C(=NH)—$NH_2$ | 2-thienyl | $CH_2$ | S | $CH_2$ |
| 2 | Me | $CH_2OH$ (R) | C(=NH)—$NH_2$ | 2-thienyl | $CH_2$ | S | $CH_2$ |
| 3 | Cl | C(=O)—NHEt (R) | C(=NH)—$NH_2$ | 2-thienyl | $CH_2$ | S | $CH_2$ |
| 4 | Cl | C(=O)—NHPr (R) | C(=NH)—$NH_2$ | 2-thienyl | $CH_2$ | S | $CH_2$ |
| 5 | Cl | C(=O)—NHiBu (R) | C(=NH)—$NH_2$ | 2-thienyl | $CH_2$ | S | $CH_2$ |
| 6 | OH | $CH_2OH$ (R) | C(=NH)—$NH_2$ | 2-thienyl | $CH_2$ | S | $CH_2$ |
| 7 | Cl | H | C(=NH)—$NH_2$ | 4-fluorophenyl | $CH_2$ | S | $CH_2$ |
| 8 | OH | H | C(=NH)—$NH_2$ | 4-fluorophenyl | $CH_2$ | S | $CH_2$ |
| 9 | OH | H | H | 2-thienyl | $CH_2$ | S | $CH_2$ |
| 10 | Cl | H | C(=NH)—$NH_2$ | 2-thienyl | $CH_2$ | S | $CH_2$ |
| 11 | Cl | C(=O)—NHcPr (R) | C(=NH)—$NH_2$ | 2-thienyl | $CH_2$ | S | $CH_2$ |
| 12 | Cl | C(=O)—NH—$CH_2$-cPr (R) | C(=NH)—$NH_2$ | 2-thienyl | $CH_2$ | S | $CH_2$ |
| 13 | Cl | C(=O)—NHBzl (R) | C(=NH)—$NH_2$ | 2-thienyl | $CH_2$ | S | $CH_2$ |
| 14 | Cl | C(=O)—NHBu (R) | C(=NH)—$NH_2$ | 2-thienyl | $CH_2$ | S | $CH_2$ |
| 15 | Cl | C(=O)—NHiPr (R) | C(=NH)—$NH_2$ | 2-thienyl | $CH_2$ | S | $CH_2$ |
| 16 | Cl | C(=O)—NHiBu (R) | C(=NH)—$NH_2$ | 2-thienyl | $CH_2$ | S | CH(OH) |
| 17 | Et | $CH_2OH$ (S) | C(=NH)—$NH_2$ | 2-thienyl | $CH_2$ | S | $CH_2$ |
| 18 | Cl | C(=O)—NHiBu (R) | C(=NH)—$NH_2$ | 2-thienyl | S | $CH_2$ | $CH_2$ |
| 19 | Cl | C(=O)—NHiBu (S) | C(=NH)—$NH_2$ | 2-thienyl | $CH_2$ | S | $CH_2$ |
| 20 | Cl | C(=O)—NHMe (R) | C(=NH)—$NH_2$ | 2-thienyl | $CH_2$ | S | $CH_2$ |
| 21 | Cl | C(=O)—$NEt_2$ (R) | C(=NH)—$NH_2$ | 2-thienyl | $CH_2$ | S | $CH_2$ |
| 22 | Cl | $CH_2OH$ (S) | C(=NH)—$NH_2$ | 2-thienyl | $CH_2$ | S | $CH_2$ |
| 23 | OH | $CH_2OH$ (S) | C(=NH)—$NH_2$ | 2-thienyl | $CH_2$ | S | $CH_2$ |
| 24 | Cl | $CH_2OH$ (R) | C(=NH)—$NH_2$ | 4-fluorophenyl | $CH_2$ | S | $CH_2$ |
| 25 | Cl | $CH_2OH$ (R) | C(=NH)—$NH_2$ | 2-thienyl | S | CH | $CH_2$ |
| 26 | Cl | C(=O)—NHiBu (R) | C(=NH)—$NH_2$ | phenyl | S | CH | $CH_2$ |
| 27 | Cl | C(=O)—NHiBu (R) | C(=NH)—$NH_2$ | 2-thienyl | S | CH | CH(OH) |
| 28 | Cl | C(=O)—NHEt (R) | C(=NH)—$NH_2$ | 2-thienyl | S | S | $CH_2$ |
| 29 | Cl | C(=O)—NHEt (R) | C(=NH)—$NH_2$ | phenyl | S | S | $CH_2$ |
| 30 | Cl | C(=O)—NHEt (R) | C(=NH)—$NH_2$ | 2-thienyl | S | CH | $CH_2$ |
| 31 | Cl | C(=O)—NHEt (R) | C(=NH)—$NH_2$ | 2-thienyl | S | CH | CH(OH) |
| 32 | Cl | C(=O)—NHEt (R) | C(=NH)—$NH_2$ | phenyl | $CH_2$ | S | CH(OH) |
| 33 | Cl | C(=O)—NHEt (R) | C(=NH)—$NH_2$ | 2-thienyl | $CH_2$ | S | S |
| 34 | Cl | C(=O)—NHEt (R) | C(=NH)—$NH_2$ | 2-thienyl | S | CH | S |
| 35 | Cl | C(=O)—NHPr (R) | C(=NH)—$NH_2$ | 2-thienyl | $CH_2$ | S | S |
| 36 | Cl | C(=O)—NH—$CH_2$-2-thienyl (R) | C(=NH)—$NH_2$ | 2-thienyl | $CH_2$ | S | S |

TABLE 1-continued
Example Compounds of the Invention.
| Compound | R² | R³ (configuration) | R⁴ | Ar | X | Y | Z |
|---|---|---|---|---|---|---|---|
| 37 | Cl | C(=O)—NH—CH₂-2-thienyl (R) | C(=NH)—NH₂ | 4-fluorophenyl | CH₂ | S | S |
| 38 | OH | C(=O)—NHBzl (R) | C(=NH)—NH₂ | 2-thienyl | CH₂ | S | CH₂ |
| 39 | Cl | C(=O)—NHBzl (R) | C(=NH)—NH₂ | 2-thienyl | CH₂ | S | S |
| 40 | Cl | H | C(=NH)—NH₂ | 2-thienyl | CH₂ | S | S |
| 41 | Cl | H | C(=NH)—NH₂ | 4-fluorophenyl | CH₂ | S | S |
Structures of Compounds 1-41:
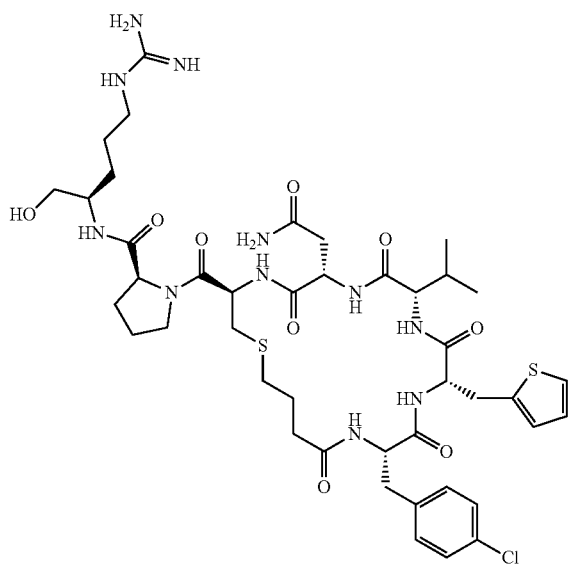
1
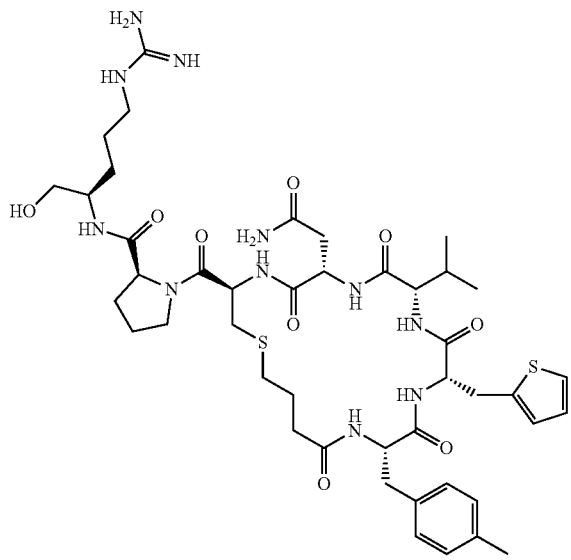
2

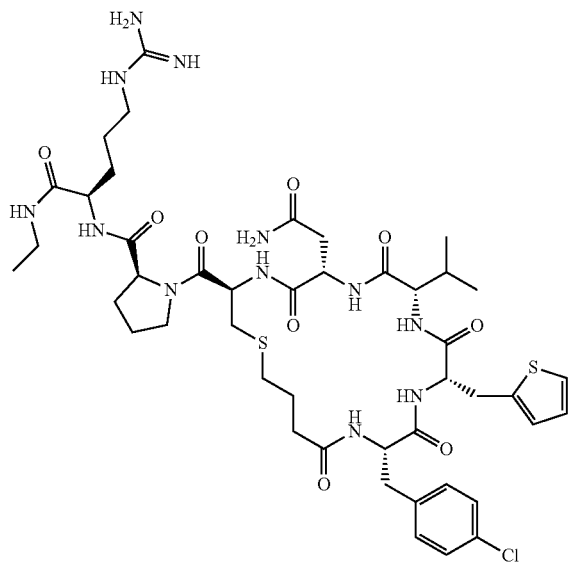
3
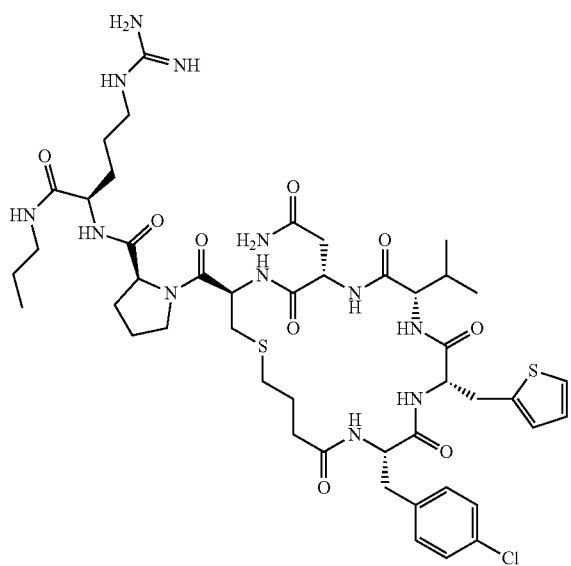
4

5
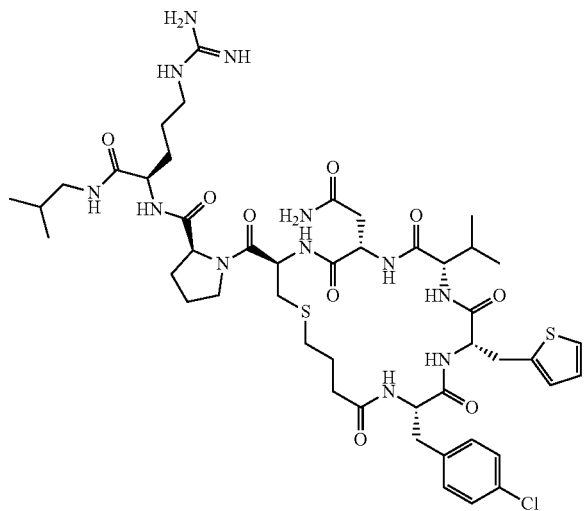
6
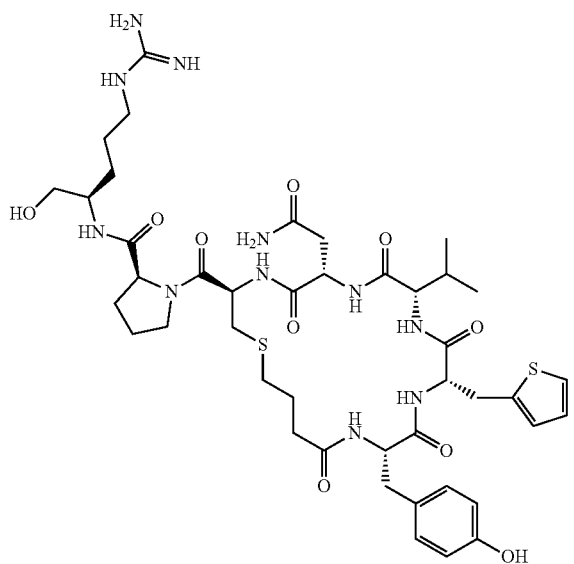

-continued
7
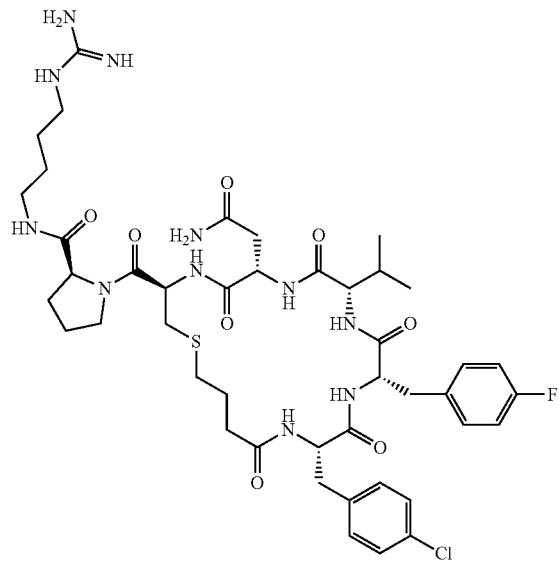
8
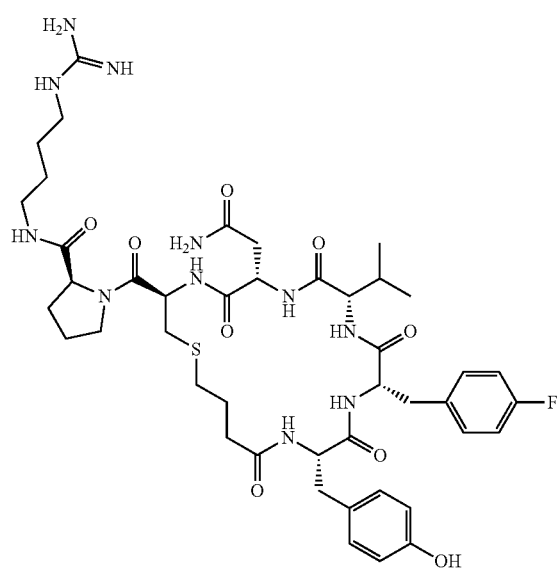

9
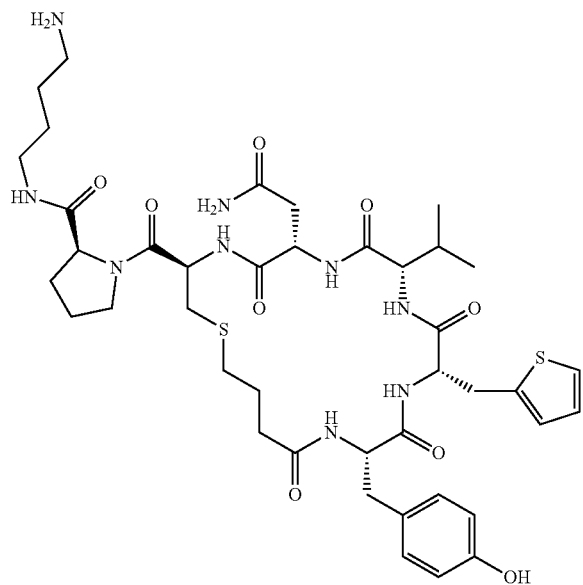
10
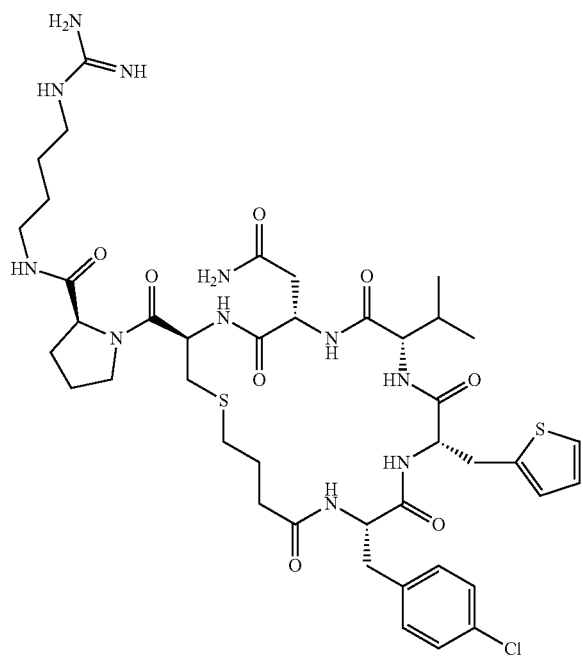

-continued
11
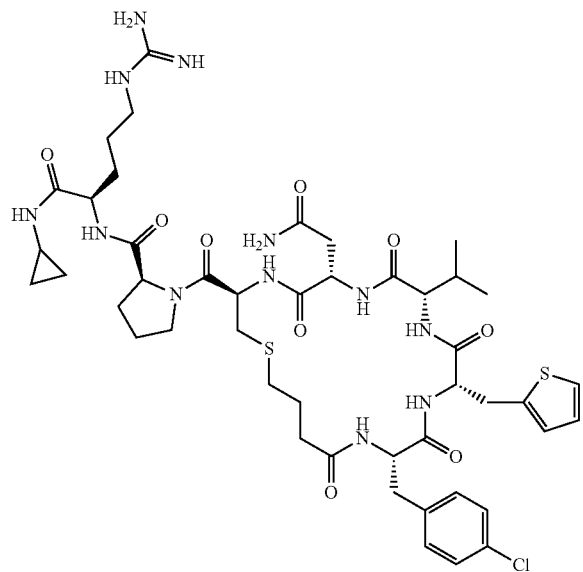
12
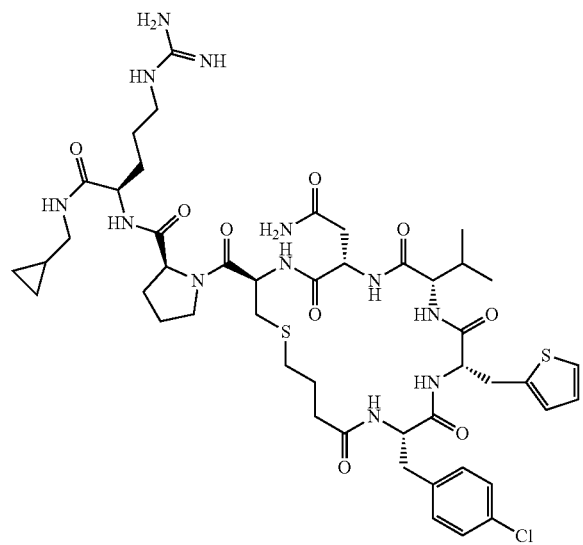

13
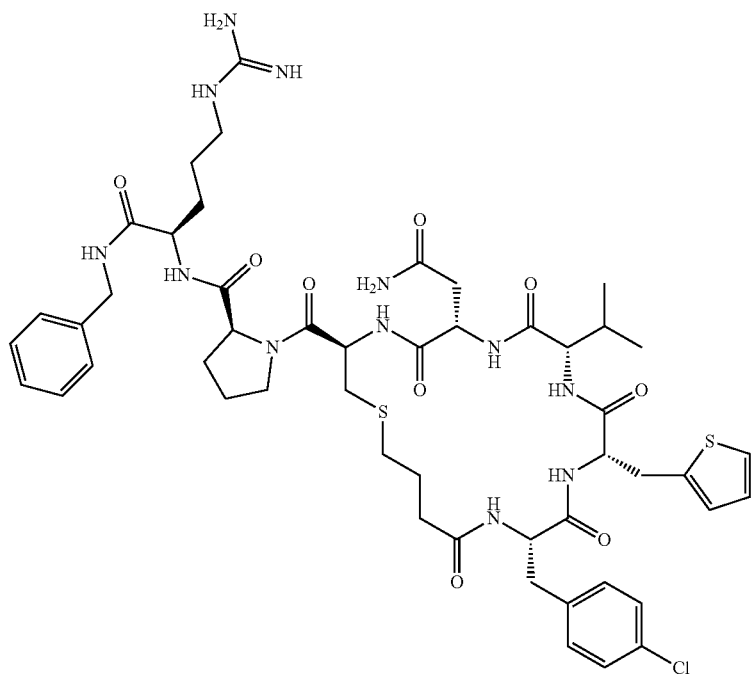
14
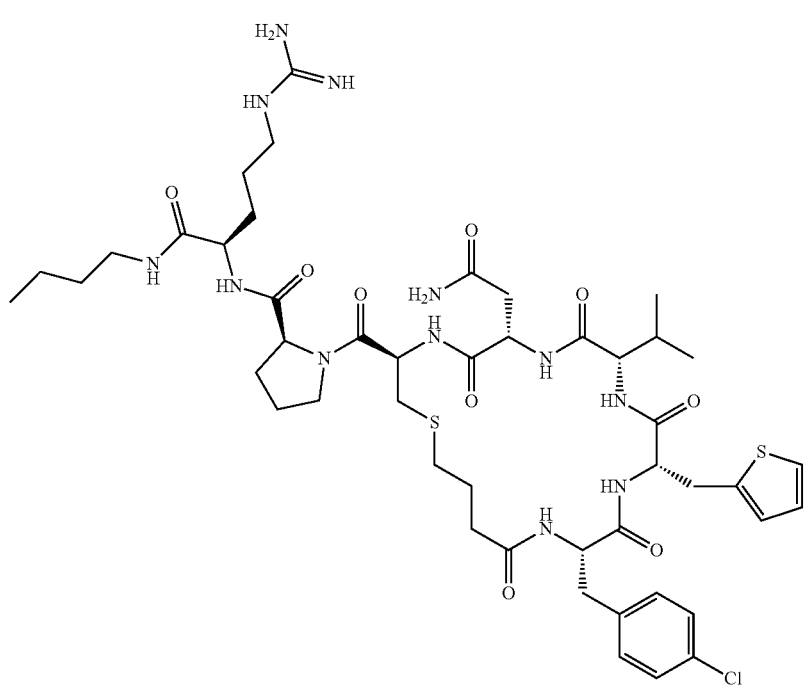

15
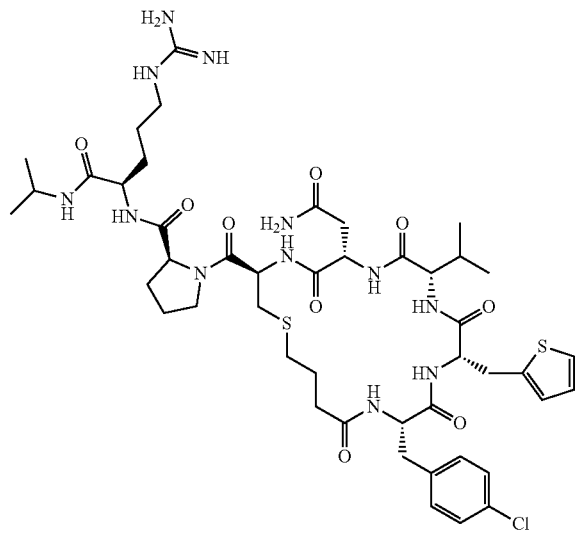
16
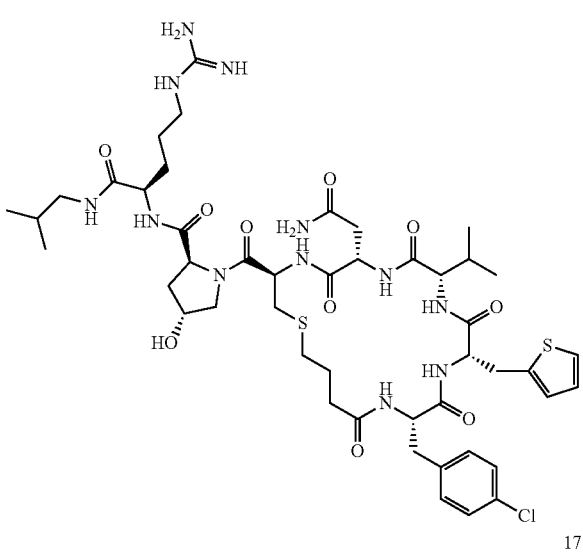
17
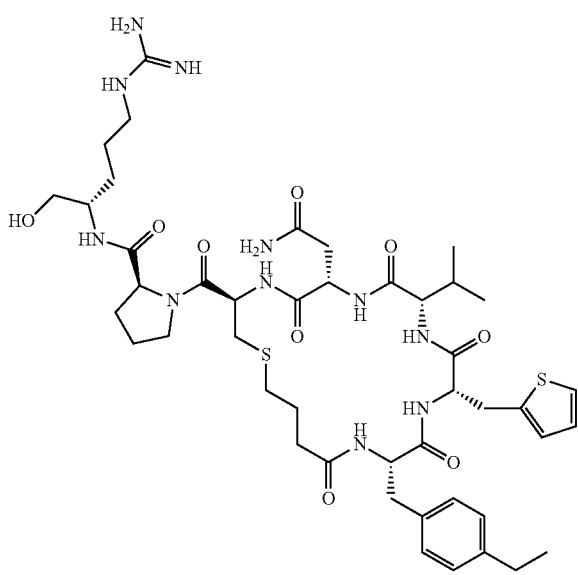

-continued
18
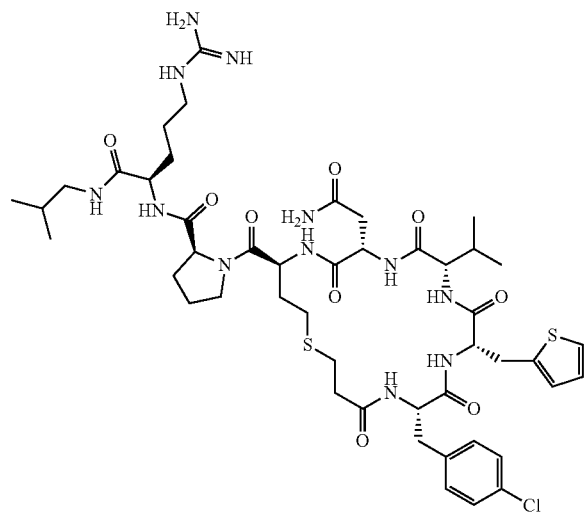
19
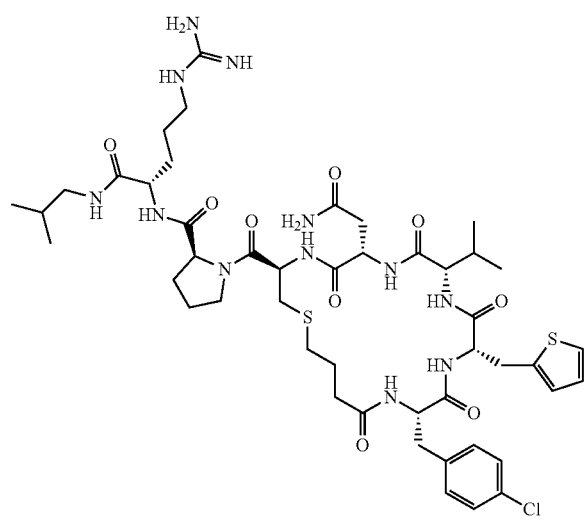
20
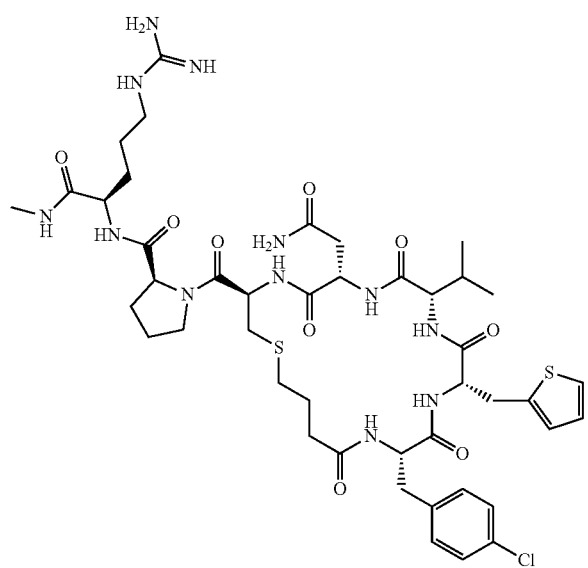

21
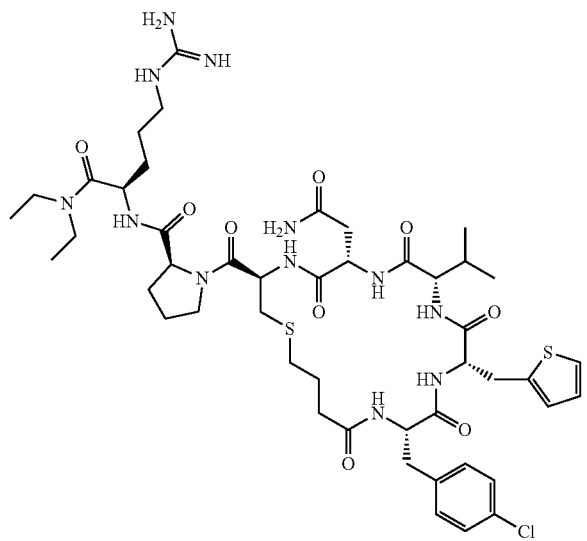
22
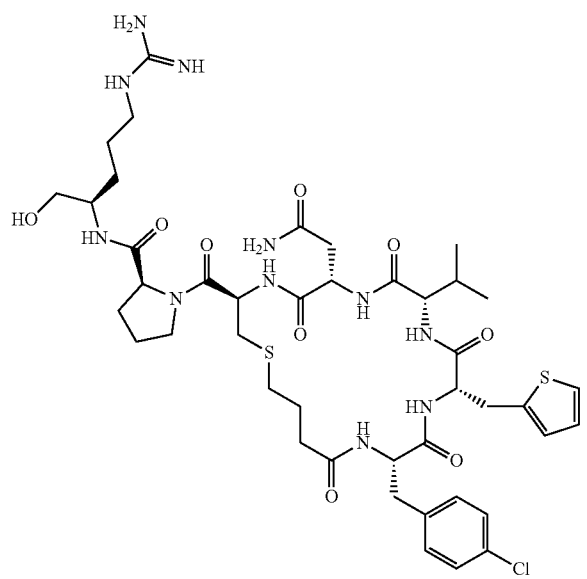

23
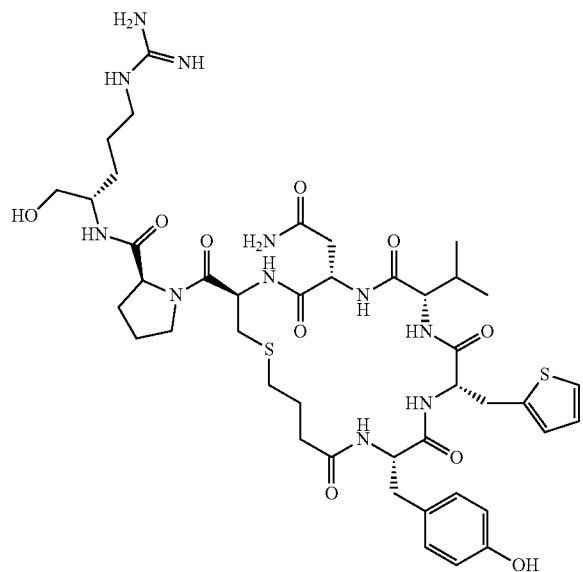
24
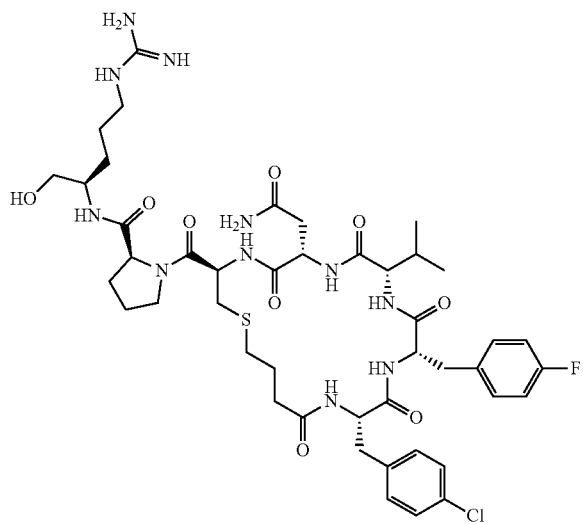

25
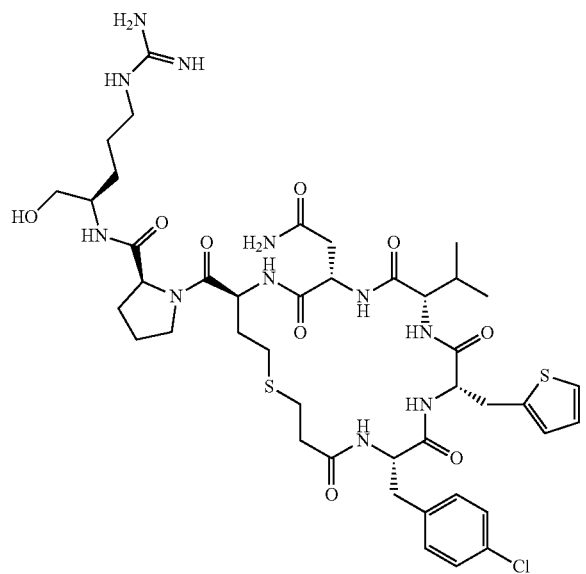
26
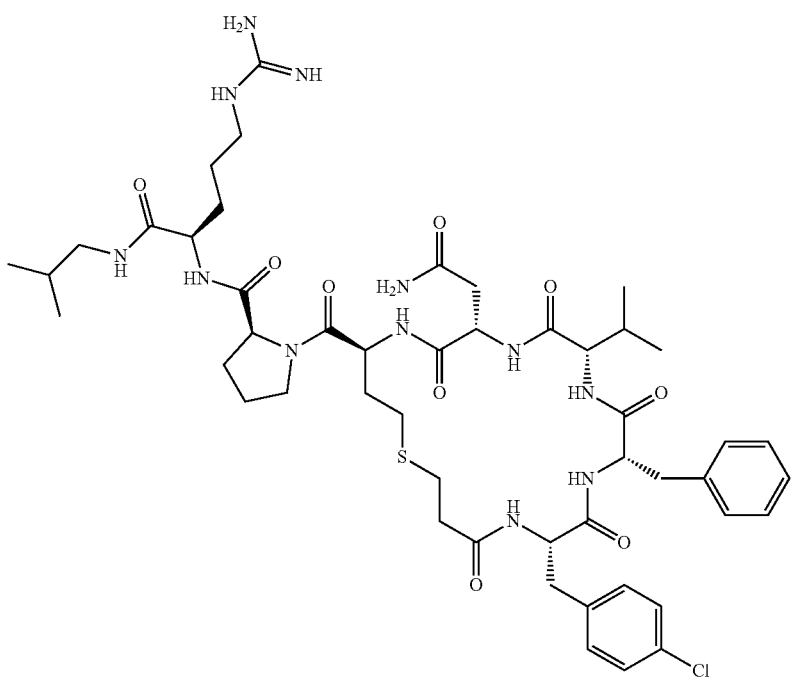

27
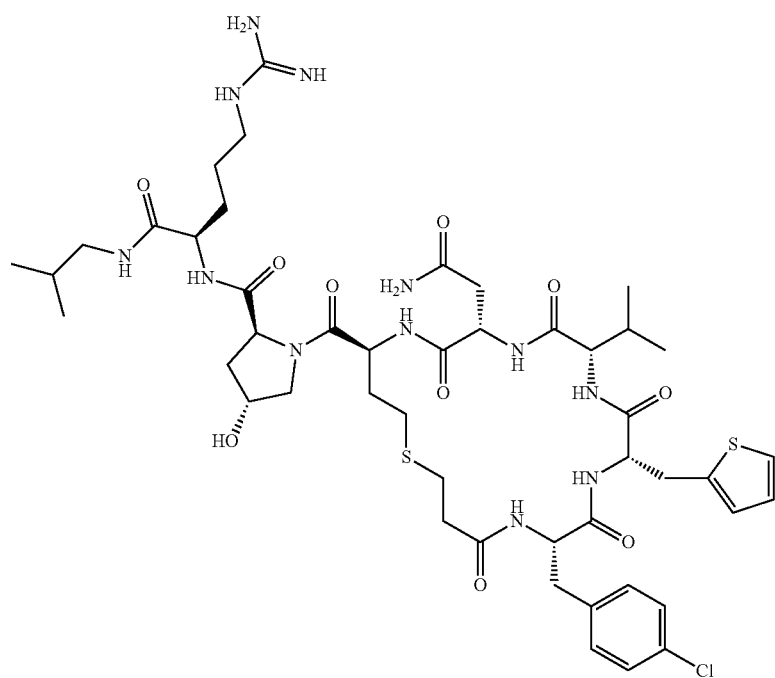
28
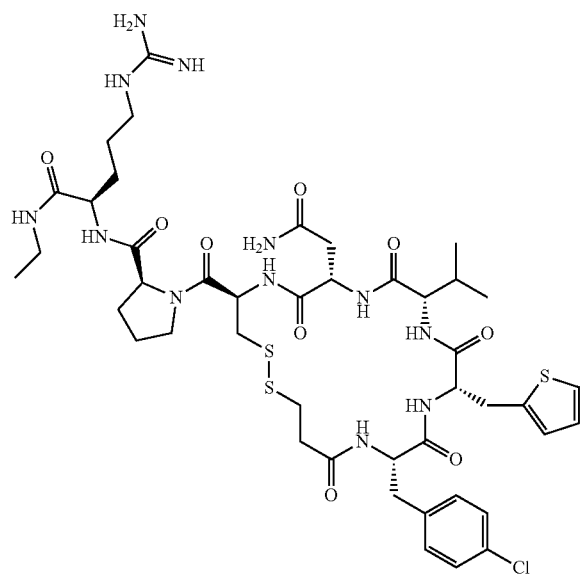

29
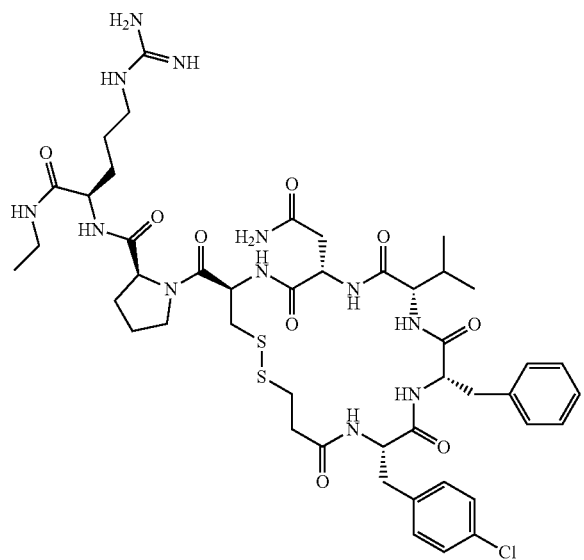
30
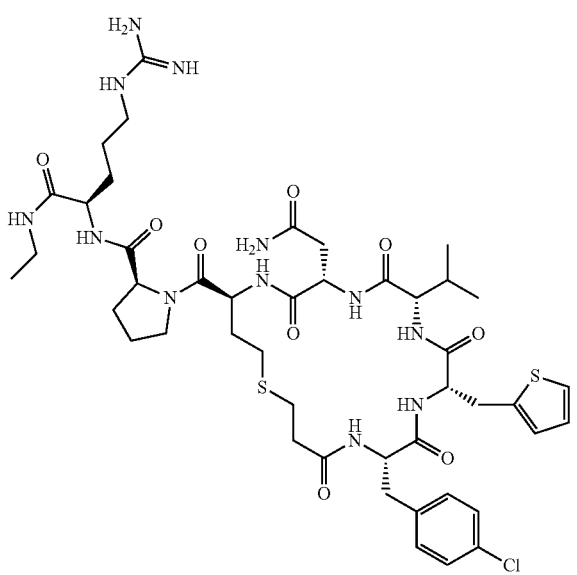

31
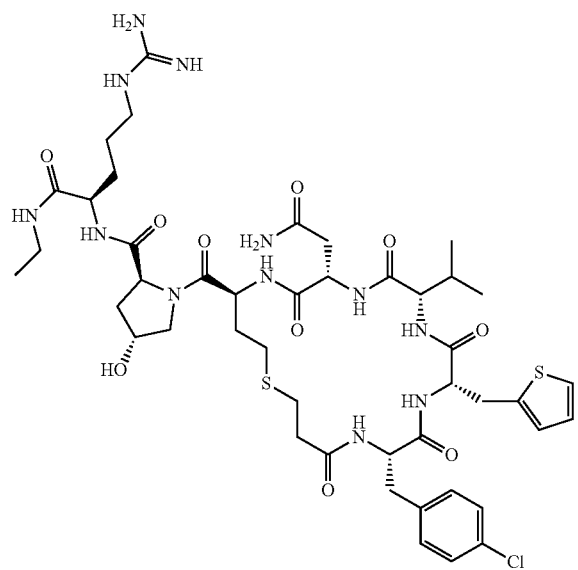
32
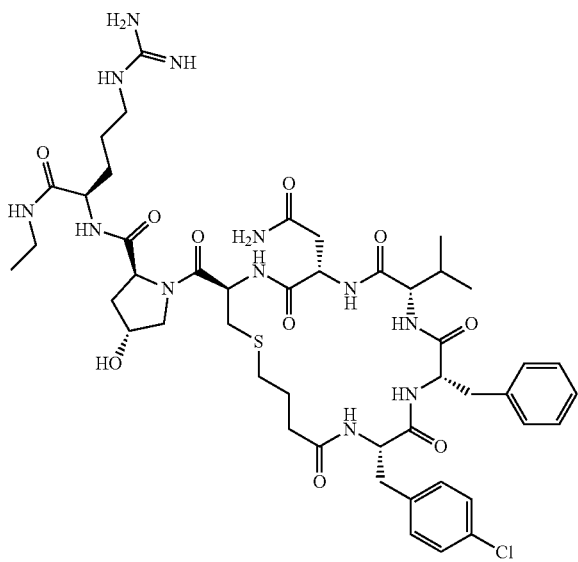

33
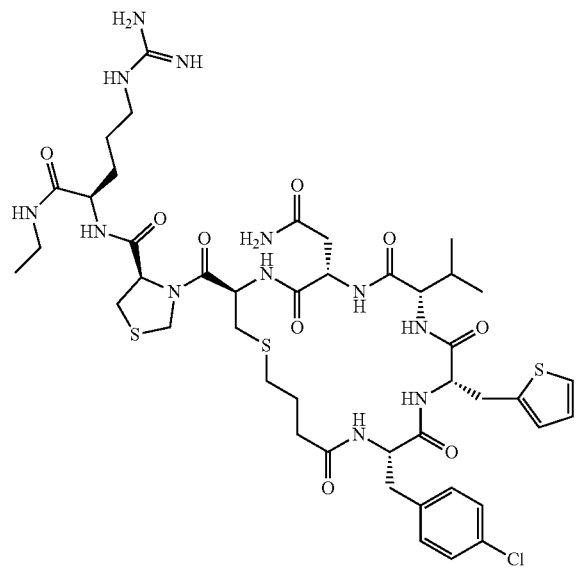
34
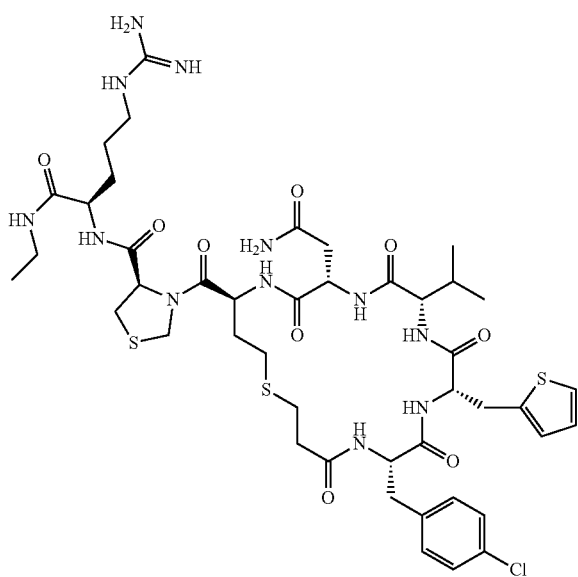

35
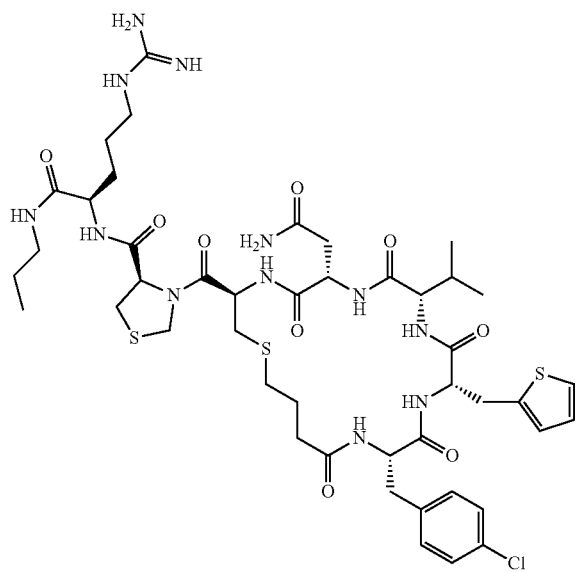
36
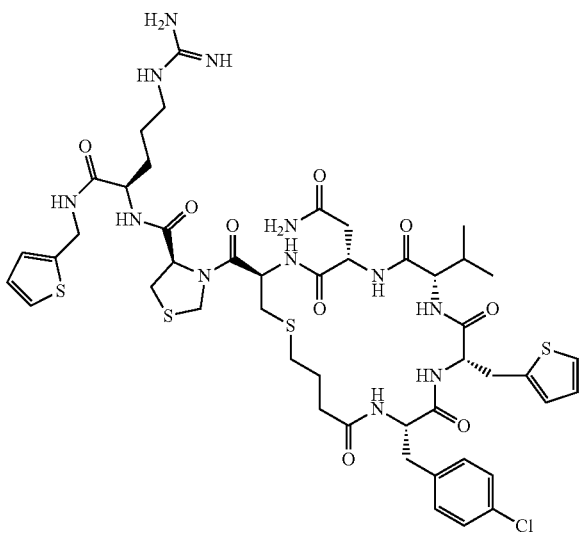

37
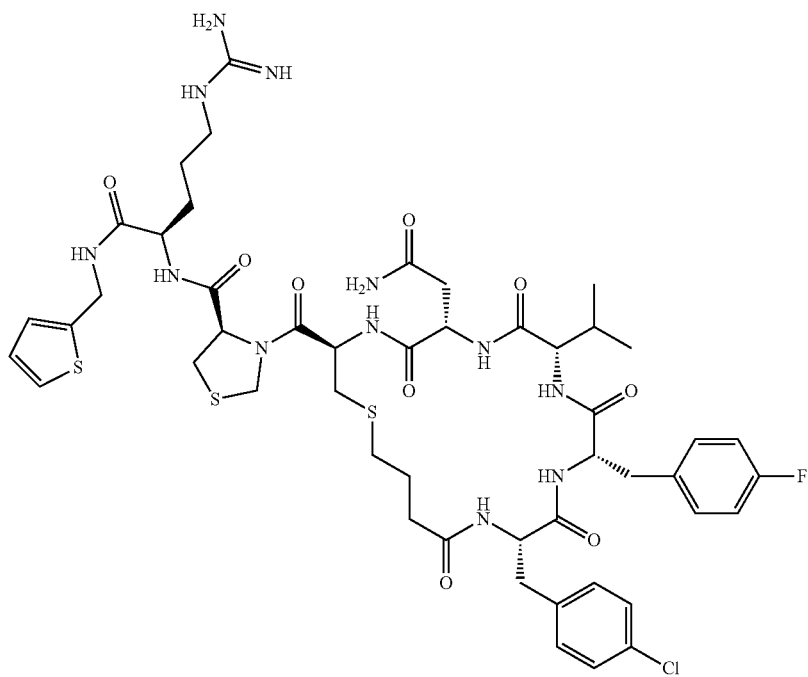
38
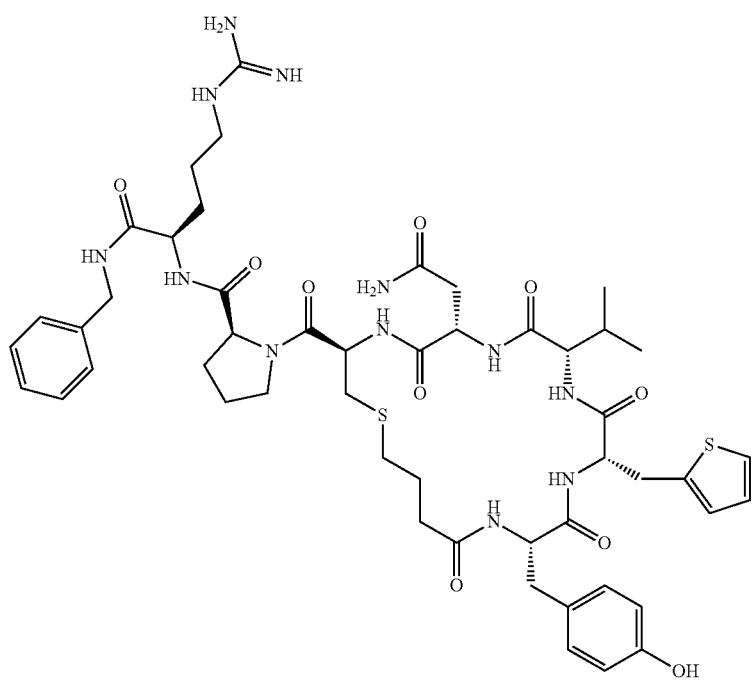

39
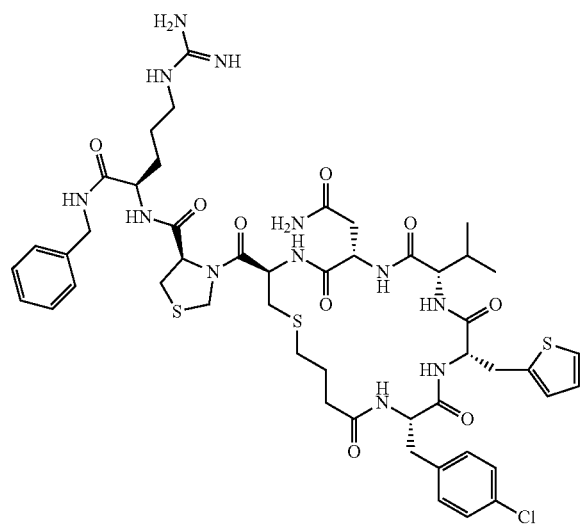
40
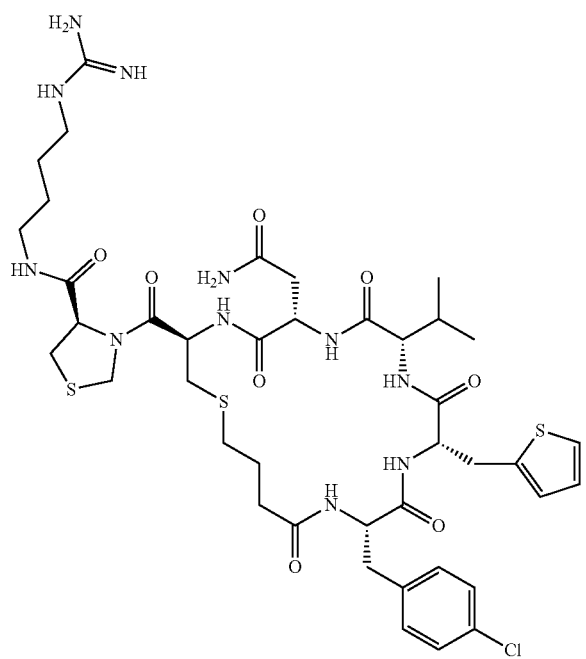

-continued
41
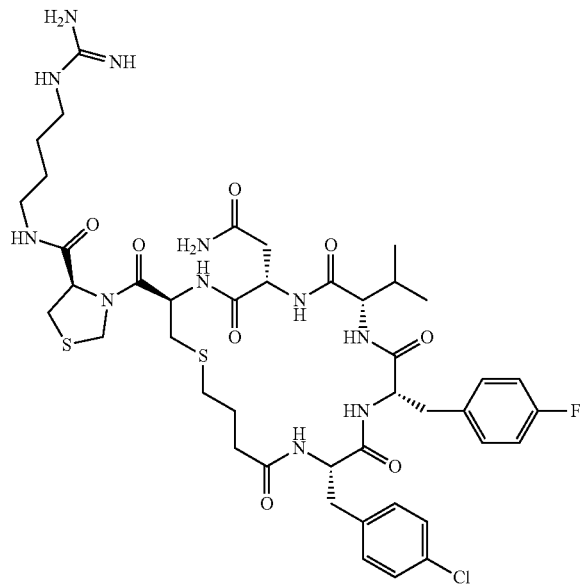
TABLE 2
Physicochemical properties of compounds 1-41
| Compound | M + H (calculated) | M + H (observed) | HPLC purity |
|---|---|---|---|
| 1 | 976.4 | 976.4 | 99.3 |
| 2 | 956.5 | 956.4 | 98.3 |
| 3 | 1017.4 | 1017.4 | 100.0 |
| 4 | 1031.4 | 1031.5 | 100.0 |
| 5 | 1045.5 | 1045.5 | 100.0 |
| 6 | 958.4 | 958.5 | 100.0 |
| 7 | 958.4 | 958.5 | 95.8 |
| 8 | 940.5 | 940.5 | 99.6 |
| 9 | 886.4 | 886.4 | 99.6 |
| 10 | 946.4 | 946.7 | 99.1 |
| 11 | 1029.4 | 1029.4 | 100.0 |
| 12 | 1043.4 | 1043.4 | 100.0 |
| 13 | 1079.4 | 1079.5 | 100.0 |
| 14 | 1045.5 | 1045.8 | 97.3 |
| 15 | 1031.4 | 1031.5 | 100.0 |
| 16 | 1061.5 | 1061.5 | 100.0 |
| 17 | 970.5 | 970.4 | 100.0 |
| 18 | 1045.5 | 1045.4 | 100.0 |
| 19 | 1045.5 | 1045.5 | 100.0 |
| 20 | 1003.5 | 1003.4 | 100.0 |
| 21 | 1045.5 | 1045.5 | 99.2 |
| 22 | 976.4 | 976.5 | 98.2 |
| 23 | 948.4 | 958.5 | 96.6 |
| 24 | 988.4 | 988.5 | 99.3 |
| 25 | 976.4 | 976.5 | 100.0 |
| 26 | 1039.5 | 1039.5 | 100.0 |
| 27 | 1061.5 | 1061.5 | 99.8 |
| 28 | 1035.4 | 1035.4 | 97.4 |
| 29 | 1029.4 | 1029.5 | 99.3 |
| 30 | 1017.4 | 107.5 | 99.5 |
| 31 | 1033.4 | 1033.5 | 99.2 |
| 32 | 1027.5 | 1027.5 | 99.2 |
| 33 | 1035.4 | 1035.5 | 100.0 |
| 34 | 1035.4 | 1035.5 | 100.0 |
| 35 | 1049.4 | 1049.7 | 99.3 |
| 36 | 1103.4 | 1103.7 | 100.0 |
| 37 | 1115.4 | 1115.7 | 99.2 |
| 38 | 1061.5 | 1061.7 | 98.3 |
| 39 | 1097.4 | 1097.7 | 96.8 |
| 40 | 964.3 | 964.6 | 99.6 |
| 41 | 976.4 | 976.7 | 100.0 |
TABLE 3
In vitro assay data for compounds 1-41
| Compound | EC50 hV2-R | % Efficacy hV2-R | EC50 hV1b-R | % Efficacy hV1b-R |
|---|---|---|---|---|
| 1 | 0.10 | 102 | 140.91 | 42 |
| 2 | 0.39 | 104 | 806.52 | 27 |
| 3 | 0.29 | 92 | 171.74 | 62 |
| 4 | 0.33 | 92 | 249.07 | 49 |
| 5 | 0.22 | 100 | 213.51 | 50 |
| 6 | 0.08 | 93 | 57.58 | 56 |
| 7 | 0.31 | 89 | 142.28 | 39 |
| 8 | 0.10 | 91 | 175.57 | 62 |
| 9 | 0.19 | 94 | >10000 | 60 |
| 10 | 0.07 | 104 | 104.64 | 42 |
| 11 | 0.23 | 86 | 480.08 | 36 |
| 12 | 0.21 | 90 | 321.63 | 43 |
| 13 | 0.19 | 100 | 149.75 | 37 |
| 14 | 0.26 | 98 | 187.54 | 36 |
| 15 | 0.45 | 81 | 576.96 | 33 |
| 16 | 0.23 | 87 | 480.92 | 26 |
| 17 | 0.35 | 110 | >10000 | 34 |
| 18 | 0.22 | 103 | >10000 | 29 |
| 19 | 0.29 | 98 | >10000 | 19 |
| 20 | 0.27 | 106 | 351.12 | 37 |
| 21 | 0.25 | 102 | 535.72 | 21 |
| 22 | 0.14 | 96 | 382.84 | 44 |
| 23 | 0.10 | 92 | 518.47 | 53 |
| 24 | 0.35 | 102 | 223.19 | 45 |
| 25 | 0.08 | 115 | 64.30 | 38 |
| 26 | 0.27 | 101 | 45.79 | 33 |
| 27 | 0.20 | 100 | 132.93 | 24 |
| 28 | 0.32 | 103 | >10000 | 20 |
| 29 | 0.38 | 103 | >10000 | 16 |

TABLE 3-continued

In vitro assay data for compounds 1-41

| Compound | EC50 hV2-R | % Efficacy hV2-R | EC50 hV1b-R | % Efficacy hV1b-R |
|---|---|---|---|---|
| 30 | 0.19 | 114 | 123.00 | 33 |
| 31 | 0.10 | 92 | 258.02 | 25 |
| 32 | 0.29 | 98 | 150.43 | 21 |
| 33 | 0.10 | 103 | 159.76 | 32 |
| 34 | 0.11 | 93 | 40.21 | 34 |
| 35 | 0.21 | 111 | 122.05 | 43 |
| 36 | 0.17 | 108 | 95.56 | 53 |
| 37 | 0.30 | 102 | 100.61 | 46 |
| 38 | 0.26 | 111 | 150.12 | 48 |
| 39 | 0.31 | 111 | 328.73 | 72 |
| 40 | 0.12 | 106 | 140.67 | 50 |
| 41 | 0.22 | 108 | 114.44 | 42 |
| 42 (dDAVP) | 0.22 | 100 | 6.59 | 100 |
| 43 ([Val4]dDAVP) | 0.05 | 89 | 24.13 | 98 |
| 44 (AVP) | 0.04 | | 5.4 | |

TABLE 4

Key to Amino Acid Nomenclature.

| Amino Acid | Position | Claim Nomenclature |
|---|---|---|
| Cpa | 2 | $R^2$ = Cl |
| Fpa | 2 | $R^2$ = F |
| Phe(4-Me) | 2 | $R^2$ = —$CH_3$ |
| Phe(4-Et) | 2 | $R^2$ = —$CH_2$—$CH_3$ |
| Thi | 3 | Ar = 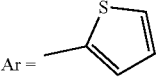 |
| Fpa | 3 | Ar = 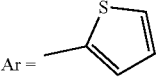 |
| Val | 4 | $R^8$ = —$CH_3$ |
| Abu | 4 | $R^8$ = —H |
| Hyp | 7 | Z = 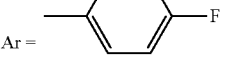 |
| Thz | 7 | Z = S |
| Agm | 8 | $R^3$ = H and $R^4$ = —C(=NH)—$NH_2$ |

EXAMPLES

General Synthesis

Amino acid derivatives were purchased from commercial providers (Aapptec, EMD Millipore and Peptides International). Resins were purchased from commercial suppliers (PCAS BioMatrix Inc. and EMD Millipore). All additional reagents, chemicals and solvents were purchased from Sigma-Aldrich and VWR.

The compounds described herein were synthesized by standard methods in solid phase peptide chemistry utilising Fmoc methodology. The peptides were assembled either manually, automatically using a Tribute Peptide Synthesizer (Protein Technologies Inc., Tucson, Ariz.) or by combination of manual and automatic syntheses.

Preparative HPLC was performed on a Waters Prep LC System using a PrepPack cartridge Delta-Pack C18, 300 Å, 15 µm, 47×300 mm at a flow rate of 100 mL/min and/or on a Phenomenex Luna C18 column, 100 Å, 5 µm, 30×100 mm at a flow rate of 40 mL/min. Analytical reverse phase HPLC was performed on an Agilent Technologies 1200rr Series liquid chromatograph using an Agilent Zorbax C18 column, 1.8 µm, 4.6×110 mm at a flow rate of 1.5 mL/min. Final compound analyses were performed on an Agilent Technologies 1200 Series chromatograph by reverse phase HPLC on a Phenomenex Gemini 110 Å C18 column, 3 µm, 2×150 mm at a flow rate of 0.3 mL/min. Mass spectra were recorded on a MAT Finningan LCQ electrospray mass spectrometer. Unless stated otherwise, all reactions were performed at room temperature. The following standard reference literature provides further guidance on general experimental set up, as well as on the availability of required starting material and reagents: Kates, S. A., Albericio, F., Eds., Solid Phase Synthesis: A Practical Guide, Marcel Dekker, New York, Basel, 2000; Greene, T. W., Wuts, P. G. M., Protective Groups in Organic Synthesis, John Wiley Sons Inc., 2nd Edition, 1991; Stewart, J. M., Young, J. D., Solid Phase Synthesis, Pierce Chemical Company, 1984; Bisello, et al., J. Biol. Chem. 1998, 273, 22498-22505; Merrifield, J. Am. Chem. Soc. 1963, 85, 2149-2154; and Chang and White P. D., 'Fmoc Solid Phase Peptide Synthesis: a Practical Approach', Oxford University Press, Oxford, 2000.

The following protecting groups were utilized to protect the given amino acid side chain functional groups: Pbf (2,2,4,6,7-pentamethyldihydrobenzofuran-5-sulfonyl) for Arg; tBu (t-butyl) for Tyr and Trt (trityl) for Cys, Gln and Asn.

Couplings of Fmoc-protected amino acids on the Tribute synthesizer were mediated with HBTU/NMM in DMF except for cysteine derivatives that were coupled with DIC/HOBt in DMF. Single cycles of 30-60 minutes with a 5-fold excess of activated Fmoc-protected amino acids were used during the synthesis. Removal of the Fmoc protecting group was monitored by UV. Multiple (up to 10 times, as needed) two-minute washes of the peptide resin with 20% piperidine in DMF were performed.

DIC/HOBt mediated couplings in DMF were employed for all amino acids in manual mode. Single cycles of at least 2 hours with a 3-fold excess of activated Fmoc-protected amino acids were used during the synthesis. The completeness of couplings was assessed with nihidrine (Kaiser) test. Removal of the Fmoc protecting group was achieved with a single 30 min. wash of the peptide resin with 20% piperidine in DMF.

Upon completion of the peptide synthesis, the peptide resins were washed with DCM and dried in vacuo. The resins were treated with TFA/$H_2O$/TIS 96:2:2 (v/v/v) for 2 h to remove the side-chain protecting groups with concomitant cleavage of the peptide from the resin. The peptides were filtered, precipitated with diethyl ether and decanted. To obtain peptides with disulfide bridges, the precipitate was dissolved in neat TFA and the solution was subsequently poured into 10% acetonitrile in water. In some cases an additional amount of acetonitrile was added to solubilize the substrate. The linear peptide was oxidized with 0.1M $I_2$/MeOH. The oxidizer solution was added dropwise until yellow color persisted. The excess of iodine was reduced with solid ascorbic acid. The pH was then adjusted to about 4 with concentrated ammonia. The obtained solution was loaded directly onto an HPLC prep column and eluted with a gradient of component B (see table below).

To cyclize peptides via amide bond formation the crude linear peptides were dissolved in DMF and a solution of HBTU in DMF was also prepared. The peptide solution and the activator solution were added interchangeably to a volume of vigorously stirred DMF containing DIPEA. The pH was maintained at 9-10 with the addition of neat DIPEA. The reaction was monitored by HPLC and typically no substrate peak was detected after the last portions of the activator and peptide solutions have been added. The reaction mixture was diluted with 0.1% AcOH and the obtained solution was loaded directly onto an HPLC prep column and eluted with a gradient of component B.

Each crude peptide was purified with buffer system T. The fractions with a purity exceeding 93%, determined by reverse-phase analytical HPLC, were pooled and reloaded onto the column and eluted with buffer T to provide trifluoroacetate salts. In some cases an additional purification with buffer system C was performed. To obtain acetate salts the fractions from runs with buffer T or C were reloaded onto the column and the column was washed with 5 volumes of 0.1 M ammonium acetate. The final product was eluted with buffer A. The fractions were pooled and lyophilized.

TABLE

Buffer Compositions

| Buffer | Component A | Component B |
|---|---|---|
| C | 0.25 M Triethylammonium Perchlorate, pH 2.3 | 60% acetonitrile, 40% Component A |
| T | 0.1% Trifluoroacetic acid (TFA) | 60% acetonitrile, 0.1% TFA |
| A | 2% Acetic acid (AcOH) | 60% acetonitrile, 2% AcOH |

The compounds prepared were typically found to be at least about 95% pure.

Example 1—Compound 21

The 1-7 fragment was assembled manually starting from 7.8 g (6.9 mmol) of H-Pro-2-chlorotrityl AM resin (EMD Millipore, catalog number 856057, 0.88 mmol/g). DIC/HOBt mediated couplings in DMF were employed. Single cycles of at least 2 hours with a 3-fold excess of activated Fmoc-protected amino acids were used during the synthesis. The completeness of couplings was assessed with ninhydrine test. Removal of the Fmoc protecting group was achieved with a single 30 min. wash of the peptide resin with 20% piperidine in DMF. The following amino acid derivatives were used to assemble residues 1-7 of the resin-bound peptide: Fmoc-Cys(($CH_2$)$_3$C(O)OtBu)-OH, Fmoc-Asn(Trt)-OH, Fmoc-Val-OH, Fmoc-Thi-OH and Boc-Cpa-OH. After the 1-7 peptide fragment was assembled the resin was washed thoroughly with DCM and treated with the DCM/HFIP 7:3 (v/v) cocktail (2×1 h, 30 mL each). The solvents were then evaporated and the residue was precipitated with ethyl ether, filtered and dried in vacuo. 5.79 g (4.63 mmol, 67%) of the crude protected linear peptide was obtained. (The remainder of this product was used in the synthesis of other compounds as described herein.)

H-D-Arg-NEt$_2$×2TFA.

2.81 g (5.4 mmol) of Boc-D-Arg(Pbf)-OH (Chem Impex, cat #05282), 1.95 mL (11.2 mmol) of DIPEA and 2.13 g (5.6 mmol) of HBTU were dissolved in 10 mL DMF. 0.62 mL (6 mmol) of diethylamine was subsequently added to the solution. No substrate was detected by analytical HPLC after 5 min. The reaction mixture was poured into 500 mL of water and the precipitate was separated by centrifugation and dried in vacuo. The residue was treated with 20 mL TFA/TIS/$H_2O$ (96/2/2, v/v/v) for 1 h and the solvents were evaporated. The residue was treated with ethyl ether and decanted. 1.65 g (3.6 mmol, 67%) of semisolid derivative was obtained which was used in the subsequent step without purification.

Coupling with H-D-Arg-NEt$_2$.

2.3 g (c.a. 1.86 mmol) of the linear protected peptide and 0.76 g (2 mmol) of HBTU were dissolved in 10 mL DMF containing 0.73 mL (4.2 mmol) DIPEA. 0.93 g (2.05 mmol) of H-D-Arg(Pbf)-OH×2TFA in 1 mL DMF was subsequently added to the reaction mixture. No substrate was detected after 5 min by HPLC. The product was precipitated with 1 L of water, filtered off and dried in vacuo. 2.6 g (1.78 mmol, 96%) of crude protected linear peptide was obtained. The fully protected peptide was treated with 20 mL TFA/TIS/$H_2O$ (96/2/2, v/v/v) for 1 h and the solvent was evaporated. The unprotected linear peptide was precipitated with ethyl ether and lyophilized. Yield 1.82 g (1.55 mmol, 83%).

The entire amount of the linear peptide was dissolved in 50 mL of DMF. A solution of 0.59 g (c.a. 1.55 mmol) HBTU in 10 mL of DMF was also prepared. The peptide solution and the activator solution were added interchangeably to 50 mL of vigorously stirred DMF containing 200 µL of DIPEA in 10 portions of 5 mL and 1 mL, respectively. The pH was maintained at 9-10 with the addition of neat DIPEA. No substrate peak was detected by HPLC after the last portions of the activator and peptide solutions have been added. The reaction mixture was diluted with 0.1% AcOH to 1 L. The obtained solution was loaded directly onto an HPLC prep column and purified with buffer system T eluted with a gradient of component B (see table above). The fractions with a purity exceeding 93%, determined by reverse-phase analytical HPLC, were pooled and reloaded onto the column. The column was washed with 5 volumes of 0.1M AcONH$_4$ and the compound was subsequently eluted with buffer C to provide acetate salt. The fractions were pooled and lyophilized. 703.1 mg (0.60 mmol, 22% overall based on 89.6% peptide content) of white peptide powder was obtained. The product purity was determined by analytical HPLC as 99.7% and the observed M+H was 1045.6 (calc. M+H=1045.5).

Example 2—Compound 10

2.32 g (about 1.8 mmol) of the protected linear peptide prepared in the synthesis of SEQ ID NO: 21 was dissolved in 7 mL of DMF and 0.63 mL (3.6 mmol, 2 eq) NMM was added followed by 0.76 g (2 mmol, 1.1 eq) HBTU. In a separate vial, 0.64 g (2.8 mmol, 1.5 eq) of agmatine sulfate was suspended in 7 mL DMF containing 0.49 mL (2.8 mmol) of DIPEA. N,O-Bis(trimethylsilyl)acetamide (BTA, Sigma-Aldrich, cat #128910) was added to the occasionally vortexed/sonicated suspension. A clear solution was obtained after 4 eq of BTA were added to the suspension. The two solutions were combined and no substrate peptide was detected by HPLC after 5 min. The product was precipitated with 1 L of water, filtered off and dried in vacuo. The resulting powder was treated with 50 mL of the TFA/TIS/$H_2O$ 96/2/2 (v/v/v) cocktail for 1.5 hrs. The solvent was evaporated and the linear peptide was precipitated with ethyl ether, reconstituted in water/acetonitrile and lyophilized.

The entire amount of peptide (2.13 g, c.a. 2 mmol) obtained in the preceding step was dissolved in 50 mL of DMF. A solution of 0.76 g (2 mmol) HBTU in 10 mL of DMF was also prepared. The peptide solution and the activator solution were added interchangeably to 50 mL of vigorously stirred DMF containing 400 µL of DIPEA in 10 portions of 2.5 mL and 0.5 mL, respectively. The pH was maintained at 9-10 with the addition of neat DIPEA. No substrate peak was detected after the last portions of the activator and peptide solutions have been added. The reaction mixture was diluted with 0.1% AcOH to 1 L and the obtained solution was loaded directly onto an HPLC prep column and purified with buffer system T eluted with a gradient of component B (see table above). The fractions with a purity exceeding 93%, determined by reverse-phase analytical HPLC, were pooled and reloaded onto the column. The column was washed with 5 volumes of 0.1M AcONH$_4$ and the compound was subsequently eluted with buffer C to provide acetate salt. The fractions were pooled and lyophilized. 656.7 mg (0.62 mmol, 23% overall yield based on 89.5% peptide content) of white peptide powder was obtained. The product purity was determined by analytical HPLC as 100.0% and the observed M+H was 946.6 (calc. M+H was 946.4).

Example 3—Compound 5

1 g (c.a. 1 mmol) of FMPB AM resin (EMD Millipore, cat #855028) was swollen in 15 ml of DCE/TMOF 1:1 mixture. To the resin suspension isobutyl amine (1.5 mL, 15 mmol) was added followed by 3.2 g solid sodium triacetoxyborohydride. The suspension was shaken overnight. The resin was washed with MeOH, DMF and DCM and was subsequently acylated with Fmoc-D-Arg(Pbf)-OH/DIC (4 eq) in DCM. The resin was washed with DMF and tested for acylation completeness with the chloranil test (negative). The resin was split into three equal portions and the synthesis was continued at 0.33 mmol scale on the Tribute Synthesizer. Single couplings mediated with HBTU/NMM in DMF or with DIC/HOBt (for Cys) with a 5-fold excess of Fmoc-protected amino acids were used. The Fmoc protecting group was removed with several consecutive 2 min. washes with 20% piperidine in DMF. The following amino acid derivatives were used in the automatic synthesis: Fmoc-Pro-OH, Fmoc-Cys((CH$_2$)$_3$C(O)OtBu)-OH, Fmoc-Asn(Trt)-OH, Fmoc-Val-OH, Fmoc-Thi-OH and Boc-Cpa-OH. After the entire peptide sequence has been assembled the peptide was cleaved from the resin with 20 mL of TFA/H$_2$O/TIS 96:2:2 (v/v/v) for 2 h. The linear peptide was dissolved in 40 mL of DMF containing 200 µL of DIPEA. A solution of 152 mg (c.a. 0.4 mmol) HBTU in 5 mL of DMF was also prepared. The peptide solution and the activator solution were added interchangeably to 40 mL of vigorously stirred DMF in 10 portions of 4 mL and 0.5 mL, respectively. The pH was maintained at 9-10 with the addition of neat DIPEA. No substrate peak was detected by HPLC after the last portion of the activator solution has been added. The reaction mixture was diluted with 0.1% AcOH to 1 L. The obtained solution was loaded directly onto an HPLC prep column. The compound was purified by three consecutive runs in buffer T.

The fractions exceeding 97% purity were pooled and lyophilized. 49.0 mg (0.042 mmol, 12% overall, assuming 90% peptide content) of white peptide powder was obtained. The product purity was determined by analytical HPLC as 99.5% and the observed M+H was 1045.6 (calc. M+H=1045.5).

Example 4—Compound 9

0.37 g (c.a. 0.3 mmol) of 1,4-diaminobutane-2-chlorotrityl resin (EMD Millipore, cat #856085) was swollen in 10 mL of DMF and the resin placed in an automatic synthesis reaction vessel. The peptide assembly was carried out on the Tribute Synthesizer. Single couplings mediated with HBTU/NMM in DMF or with DIC/HOBt (for Cys) with a 5-fold excess of Fmoc-protected amino acids were used. The Fmoc protecting group was removed with several consecutive 2 min. washes with 20% piperidine in DMF. The following amino acid derivatives were used in the automatic synthesis: Fmoc-Pro-OH, Fmoc-Cys((CH$_2$)$_3$C(O)OtBu)-OH, Fmoc-Asn(Trt)-OH, Fmoc-Val-OH, Fmoc-Thi-OH and Boc-Tyr(tBu)-OH. After the entire peptide sequence has been assembled the peptide was cleaved from the resin with 30 mL of HFIP/DCM 3:7 (v/v) for 2 h. The resin was filtered and the solvents were evaporated. The linear protected peptide was precipitated with anhydrous ethyl ether. The precipitate was decanted and suspended in 20 mL acetonitrile. 111 mg (0.4 mmol) of Z(2-Cl)-OSu and 0.136 mL (0.8 mmol) DIPEA were subsequently added to the suspension. After the substrate has dissolved, the solvent was evaporated and the residue was treated with 20 mL of the TFA/TIS/H$_2$O 95/2.5/2.5 cocktail for 1.5 h. TFA was then evaporated and the residue was precipitated with diethyl ether. The crude linear peptide was dissolved in 100 mL of DMF containing 200 µL of DIPEA. A solution of 120 mg (0.31 mmol) HBTU in 5 mL of DMF was subsequently added to the vigorously stirred reaction mixture. After 30 min. the reaction mixture was diluted with 1 L 0.1% AcOH and the obtained solution was uploaded onto prep HPLC column. The cyclic peptide was eluted with fast (c.a. 3% MeCN/min.) in buffer system T. Fractions exceeding 97% purity by analytical HPLC were pooled and lyophilized. The liophilizate was treated with 5 mL of the TMSBr/thioanisole/TFA cocktail (1/1/6, v/v/v) for 1 h at 0° C. TFA was evaporated and the peptide was precipitated with ethyl ether. The final product was purified by a single run in buffer T.

The fractions exceeding 97% purity were pooled and lyophilized. 77.5 mg (0.079 mmol, 26% overall, assuming 90% peptide content) of white peptide powder was obtained. The product purity was determined by analytical HPLC as 99.6% and the observed M+H was 886.4 (calc. M+H=886.4).

Example 5—Compound 17

0.43 g (c.a. 0.3 mmol) of H-Arg(Pbf)-O-2-chlorotrityl resin (EMD Millipore, cat #856067) was swollen in 10 mL of DMF and the resin placed in an automatic synthesis reaction vessel. The peptide assembly was carried out on the Tribute Synthesizer. Single couplings mediated with HBTU/NMM in DMF or with DIC/HOBt (for Cys) with a 5-fold excess of Fmoc-protected amino acids were used. The Fmoc protecting group was removed with several consecutive 2 min. washes with 20% piperidine in DMF. The following amino acid derivatives were used in the automatic synthesis: Fmoc-Pro-OH, Fmoc-Cys((CH$_2$)$_3$C(O)OtBu)-OH, Fmoc-Asn(Trt)-OH, Fmoc-Val-OH and Fmoc-Thi-OH. After the 3-8 peptide sequence has been assembled Fmoc-Phe(4-Et)-OH was coupled manually using DIC/HOBt method with 2-fold excess of reagents. The Fmoc group was then replaced with the Boc group by treating the resin with 20% PIP/DMF for 30 min. and acylating the N-terminal amino function with Boc$_2$O in DMF. The linear peptide was cleaved from the resin with 30 mL of HFIP/DCM 3:7 (v/v) for 2 h. The resin was filtered and the solvents were evaporated. The linear protected peptide was precipitated with anhydrous ethyl ether. The precipitate was decanted and dried in vacuo. 450 mg of the crude protected peptide was obtained. The entire amount of the peptide (c.a. 0.3 mmol) was dissolved in 10 mL 1,2-dichloroethane containing 0.5 mL DMF and 61 µL (0.45 mmol) NMM. The solution was cooled to 0° C. on ice bath and 61 µL (0.45 mmol) of isobutyl chloroformate was added. The reaction mixture was magnetically stirred for 10 min. at 0° C. A solution of 160 mg (4.5 mmol) sodium borohydride in 5 mL water was added in one portion. The reaction was diluted with 200 mL water and the product was separated by centrifugation and dried in vacuo. The product was then was treated with 20 mL of the TFA/TIS/H$_2$O 95/2.5/2.5 cocktail for 1.5 h. TFA was then evaporated and the residue was precipitated with diethyl ether. The crude linear peptide was dissolved in 80 mL of DMF containing 200 µL of DIPEA. A solution of 61 mg (0.15 mmol) HBTU in 5 mL of DMF was subsequently added to the vigorously stirred reaction mixture. After 30 min. the reaction mixture was diluted with 1 L 0.1% AcOH and the obtained solution was uploaded onto prep HPLC column. The cyclic peptide was purified by two consecutive runs in buffer T.

The fractions exceeding 97% purity were pooled and lyophilized. 41.7 mg (0.039 mmol, 13% overall, assuming 90% peptide content) of white peptide powder was obtained. The product purity was determined by analytical HPLC as 95.1% and the observed M+H was 970.6 (calc. M+H=970.5).

Experimental (Biological Testing)

In Vitro Receptor Assays
V$_2$ Receptor Activity

Agonist activity of compounds on the human V$_2$ receptor (h V$_2$R) was determined in a transcriptional reporter gene assay by transiently transfecting an h V$_2$ receptor expression DNA into HEK-293 (human embryonic kidney 293 cell line) cells in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 h, followed by lysis of cells, determination of luciferase activity, and determination of compound efficacies and EC$_{50}$ values through non-linear regression. Desmopressin (dDAVP) was used as an internal control in each experiment. Results for the tested compounds are shown in Table 3

V$_{1b}$ Receptor Activity

To determine selectivity, compounds were tested in luciferase-based transcriptional reporter gene assays expressing the human V$_{1b}$ receptor (hV$_{1b}$R). Agonist activity of compounds on the hV$_{1b}$R was determined in a transcriptional reporter gene assay in a Flp-In™ 293 cell line (HEK-flpin) stably transfected to express the hV$_{1b}$R. These cells are transiently transfected with an NFAT responsive elements-luciferase (NFAT-Luc) reporter. Cells were exposed to serial dilutions of compounds diluted 10-fold per dose for 5 hours, followed by lysis of cells, determination of luciferase activity, and determination of compound efficacies and EC$_{50}$ values through non-linear regression. AVP was used as an internal control in each experiment. Results for the tested compounds are shown in Table 3.

Renal Clearance

Desmopressin is cleared from the body primarily by the kidneys ("renal clearance"). Compounds of the invention have a higher extent of clearance through non-renal mechanisms. Pharmacokinetic experiments were performed in nephrectomized and sham-operated rats. Non-renal clearance (CLnr) was determined in nephrectomized rats, and total clearance was determined in sham-operated rats (CLsham). % Non-Renal Clearance was calculated by (CLnr/CLsham)×100.

For the pharmacokinetic studies, adult male Sprague Dawley rats were catheterized via the jugular vein (for compound administration) and carotid artery (for blood collection). A solution containing multiple compounds (cassette dosing) was injected into the jugular vein catheter (0.1 mg FB/ml of each compound, 0.3 ml/animal; nominal dose of 0.1 mg FB/kg/compound). Blood samples were collected at 2, 6, 10, 15, 20, 30, 45, 60, 90, and 120 minutes post-administration using an automated blood sampling system, the Instech Laboratories Automated Blood Sampling Unit 2nd generation (ABS2). Plasma was prepared from whole blood using K2EDTA as anticoagulant. Subsequent bioanalysis of samples included compound extraction and plasma concentration determination using standard LC/MS methods. Analyte concentration was calculated from peak areas and calibration curves. PK parameters were obtained by best fitting of the compound concentration-time profile for each animal by means of a noncompartmental analysis method using WINNONLIN™ v6.3 software (Pharsight Corporation).

Antidiuresis

Compounds were tested for antidiuretic activity in a rat model. In brief, catheterized euvolemic Sprague Dawley rats were placed in metabolic cages. Each metabolic cage was set up for continuous measurement of spontaneous urine output via force transducers placed above the urine collection vials to monitor and record the time course of urine output using NOTOCORD™ software. The rats received an intravenous infusion of test compound or vehicle for three hours using a syringe pump and swivel/tether method. Data for urine output was collected during the administration of compound (0-3 hours) and was collected for the 5 hours post-administration. In some cases, urine osmolality was also determined. Compounds of the invention showed antidiuretic activity.

Pharmaceutical Compositions

There is also provided the use of a compound of formula (I), as defined herein, as a pharmaceutical. Further provided a pharmaceutical composition comprising a compound of formula (I), as defined herein, as active ingredient in association with a pharmaceutically acceptable adjuvant, diluent or carrier.

The pharmaceutical composition may be adapted for various modes of administration including for example, oral and nasal. The composition may thus for instance be in the form of tablets, capsules, powders, microparticles, granules, syrups, suspensions and solutions.

The pharmaceutical composition may optionally comprise e.g. at least one further additive selected from a disintegrating agent, binder, lubricant, flavouring agent, preservative, colourant and any mixture thereof. Examples of such and other additives are found in '*Handbook of Pharmaceutical Excipients*'; Ed. A. H. Kibbe, 3$^{rd}$ Ed., American Pharmaceutical Association, USA and Pharmaceutical Press UK, 2000.

Methods of Treatment

In a further aspect the present invention provides the use of a compound as outlined above for the manufacture of a medicament for treatment of diabetes insipidus, primary nocturnal enuresis, and nocturia. Further, methods of treating diabetes insipidus, primary nocturnal enuresis, and nocturia are provided. As used herein 'treatment' means the alleviation of symptoms, postponement of the onset of the disease and/or the cure of the disease when a compound of the invention is administered in a suitable dose.

The typical dosage of the compounds according to the present invention varies within a wide range and will depend on various factors such as the individual needs of each patient and the route of administration. The dosage may be administered once daily or more frequently than once daily, e.g. intermittently. A physician of ordinary skill in the art will be able to optimize the dosage to the situation at hand.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A vasopressin-2 receptor agonist of formula I:

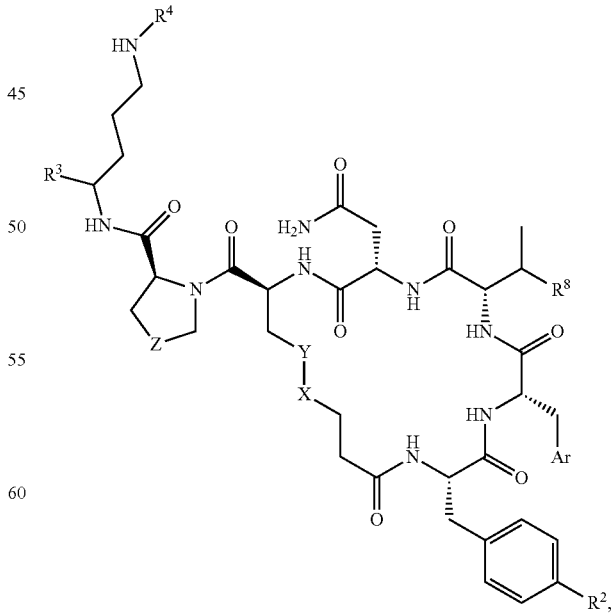

(formula I)

or a pharmaceutically acceptable salt thereof, wherein:
R² is halogen;
R³ is —C(O)—NR⁵R⁶;
R⁴ is C(=NH)—NH₂;
R⁵ and R⁶ are independently H, isobutyl, —CH2-phenyl, butyl, or ethyl, with the proviso that R⁵ and R⁶ are not both H;
X is —CH₂—;
Y is —S—;
Z is —CHR⁷— or —S—, wherein R⁷ is H;
R⁸ is —CH₃; and
Ar is thiophene.

2. The vasopressin-2 receptor agonist of claim 1, wherein both of R⁵ and R⁶ are —CH₂CH₃.

3. The vasopressin-2 receptor agonist of claim 1, wherein R² is —Cl.

4. The vasopressin-2 receptor agonist of claim 1, wherein R² is —F.

5. A pharmaceutical composition comprising a vasopressin-2 receptor agonist according to claim 1 and a pharmaceutically acceptable carrier.

6. The vasopressin-2 receptor agonist of claim 1, selected from compound 5:

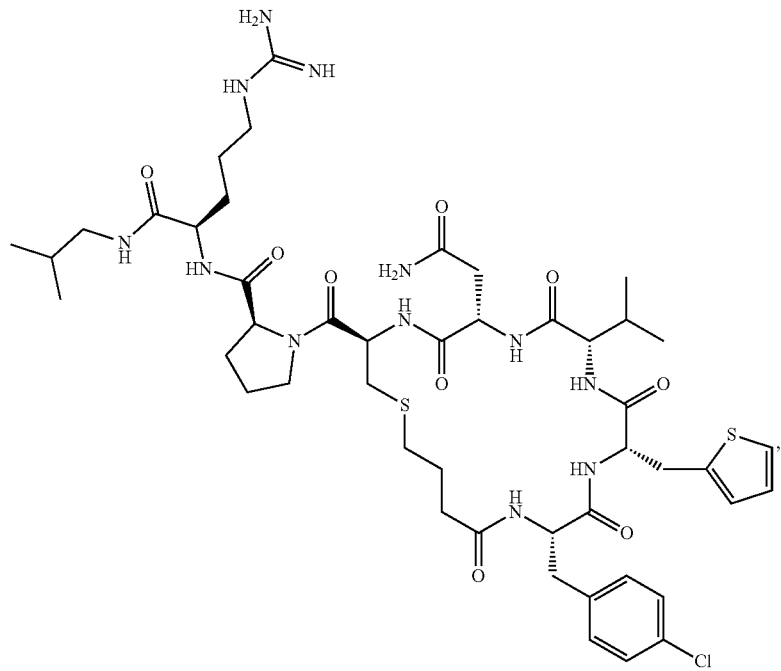

compound 13

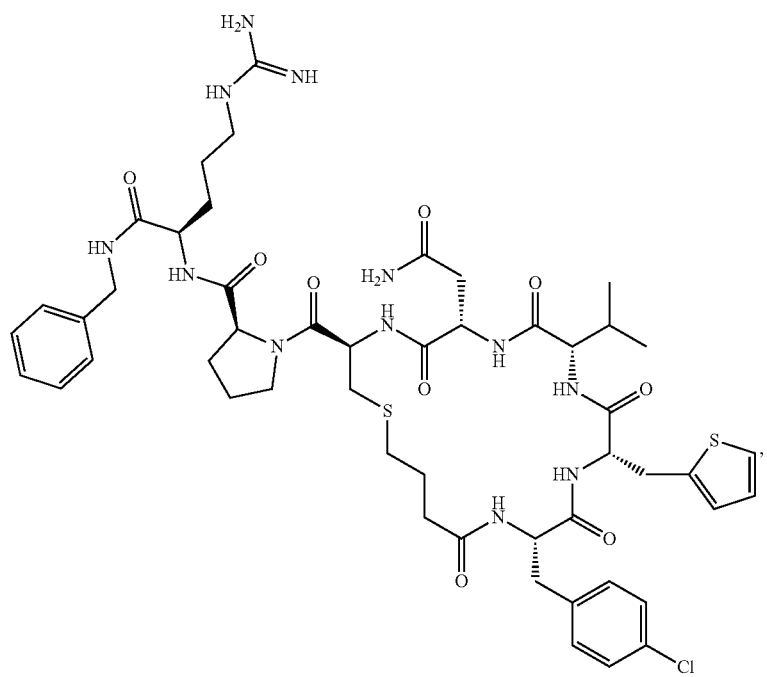

compound 14

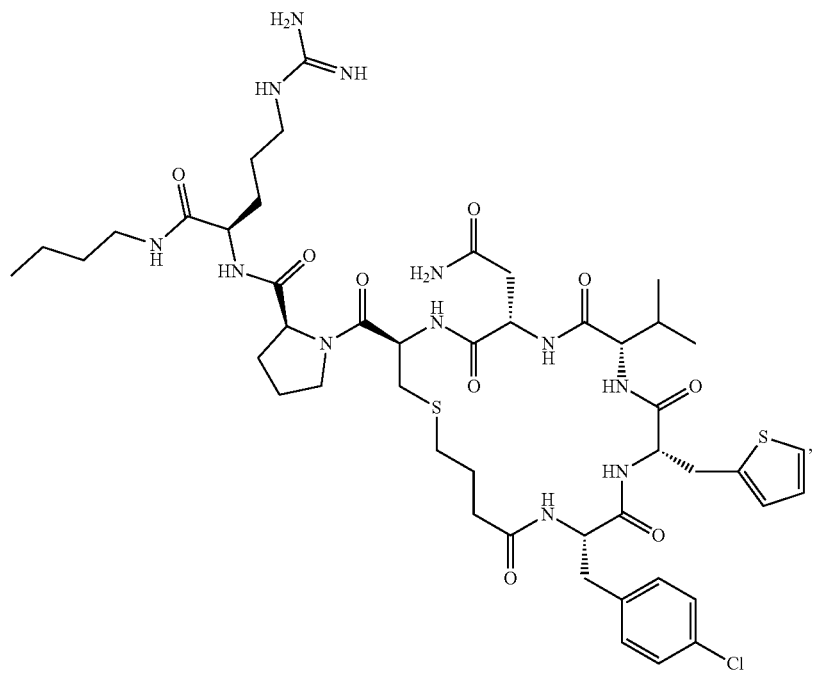
compound 21
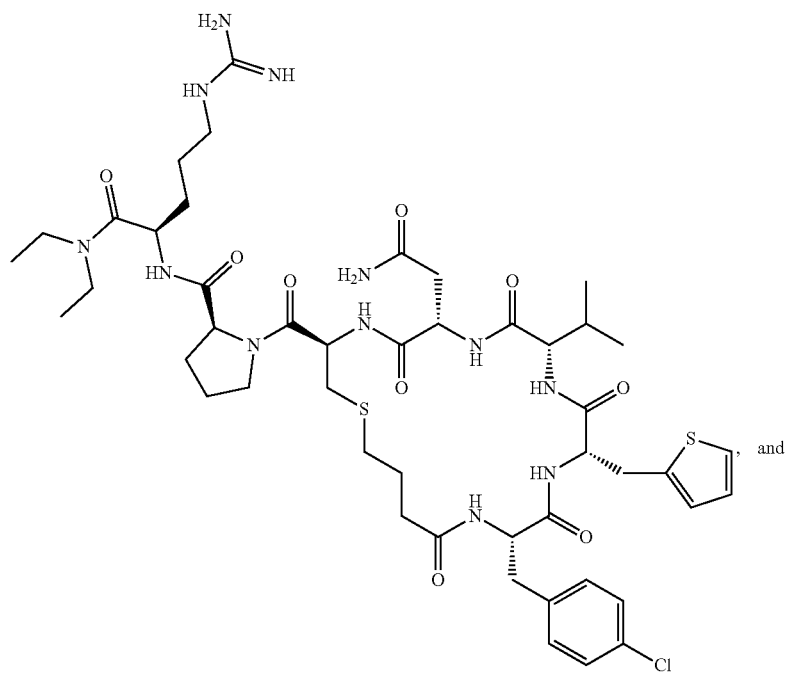
compound 33

-continued

33

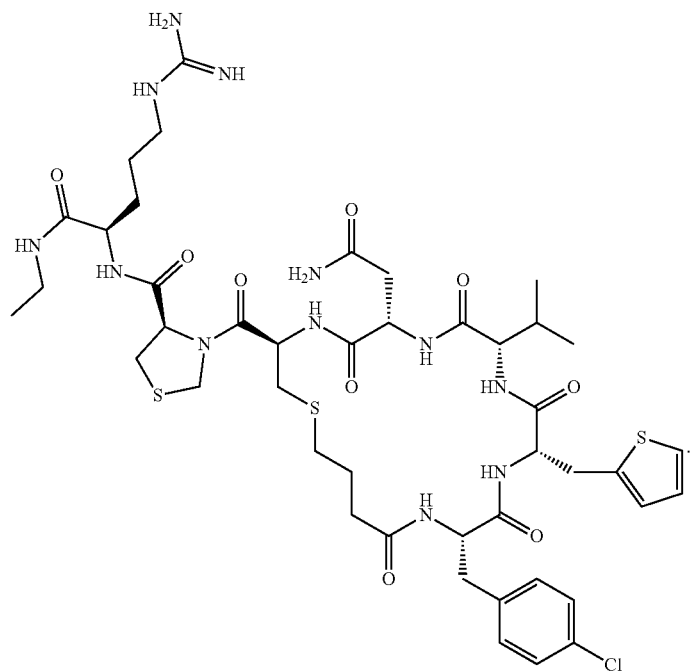

7. The vasopressin-2 receptor agonist of claim 1, wherein the agonist exhibits reduced activity at the $V_{1b}$ receptor as compared to desmopressin.

8. A method of treating diabetes insipidus, primary nocturnal enuresis, or nocturia, comprising administering a therapeutically effective amount of a vasopressin-2 receptor agonist of claim 1 to a patient in need thereof.

* * * * *

UNITED STATES PATENT AND TRADEMARK OFFICE
CERTIFICATE OF CORRECTION

PATENT NO. : 10,745,443 B2
APPLICATION NO. : 16/145073
DATED : August 18, 2020
INVENTOR(S) : Kazimierz Wisniewski et al.

Page 1 of 1

It is certified that error appears in the above-identified patent and that said Letters Patent is hereby corrected as shown below:

In the Claims

Claim 1, at Column 61, Line 4, please delete:
"$R^4$ is C(=NH)—$NH_2$"

And insert:
--$R^4$ is —C(=NH)–$NH_2$--

Signed and Sealed this
Eighth Day of December, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Disulfide bridge
<220> FEATURE:
<221> NAME/KEY: MISC_FEATURE
<222> LOCATION: (9)..(9)
<223> OTHER INFORMATION: C-term amidated

<400> SEQUENCE: 1

Cys Tyr Phe Gln Asn Cys Pro Arg Gly
1               5
```